(12) United States Patent
De Canck et al.

(10) Patent No.: US 8,426,129 B2
(45) Date of Patent: Apr. 23, 2013

(54) METHOD FOR TYPING HLA ALLELES

(75) Inventors: Ilse De Canck, Antwerp (BE); Guy Mersch, Ghent (BE); Rudi Rossau, Ekeren (BE)

(73) Assignee: Innogenetics N.V., Ghent (BE)

( * ) Notice: Subject to any disclaimer, the term of this patent is extended or adjusted under 35 U.S.C. 154(b) by 569 days.

(21) Appl. No.: 12/102,281

(22) Filed: Apr. 14, 2008

(65) Prior Publication Data

US 2010/0099081 A1   Apr. 22, 2010

Related U.S. Application Data

(62) Division of application No. 10/334,488, filed on Dec. 30, 2002, now abandoned, which is a division of application No. 09/673,809, filed as application No. PCT/EP99/02614 on Apr. 19, 1999, now Pat. No. 6,528,261.

(30) Foreign Application Priority Data

Apr. 20, 1998   (EP) ..................................... 98870088

(51) Int. Cl.
| C12Q 1/68 | (2006.01) |
| C12P 19/34 | (2006.01) |
| C07H 21/04 | (2006.01) |
| C07H 21/02 | (2006.01) |

(52) U.S. Cl.
USPC ... 435/6.11; 536/23.1; 536/24.31; 536/24.33; 435/91.1

(58) Field of Classification Search ........................ None
See application file for complete search history.

(56) References Cited

U.S. PATENT DOCUMENTS

| 4,683,195 | A | | 7/1987 | Mullis et al. |
| 5,451,512 | A | | 9/1995 | Apple et al. |
| 5,541,065 | A | * | 7/1996 | Erlich et al. ............. 435/6 |
| 5,545,526 | A | | 8/1996 | Baxter-Lowe |
| 5,550,039 | A | | 8/1996 | Trachtenberg |
| 5,567,809 | A | | 10/1996 | Apple et al. |
| 6,030,775 | A | | 2/2000 | Yang et al. |

FOREIGN PATENT DOCUMENTS

| DE | 4411594 | | 12/1995 |
| DE | 19740339 | | 3/1999 |
| EP | 237362 | | 9/1987 |
| EP | 354580 | | 2/1990 |
| EP | 0414469 B1 | | 2/1991 |
| EP | 0443748 B1 | | 8/1991 |
| EP | 472399 | | 2/1992 |
| EP | 540997 | | 5/1993 |
| JP | 8-66197 | | 3/1996 |
| WO | WO 92/08117 | | 5/1992 |
| WO | WO 92/10589 | | 6/1992 |
| WO | WO 92/19771 | | 11/1992 |
| WO | WO 93/09245 | | 5/1993 |
| WO | WO 94/06813 | | 3/1994 |
| WO | WO 94/21818 | * | 9/1994 |
| WO | WO 95/31472 | | 11/1995 |
| WO | WO 96/40989 | | 12/1996 |
| WO | WO 97/20070 | * | 6/1997 |
| WO | WO-97/20197 A2 | | 6/1997 |
| WO | WO-97/23645 | | 7/1997 |
| WO | WO-97/23650 A2 | | 7/1997 |
| WO | WO-98/26091 A2 | | 6/1998 |
| WO | WO-99/07883 A1 | | 2/1999 |
| WO | WO-99/19509 A2 | | 4/1999 |
| WO | WO-99/54496 | | 10/1999 |

OTHER PUBLICATIONS

Garber, Theodore et al. HLA-B alleles of the Cayapa of Ecuador: new B39 and B15 alleles. 1995 Immunogenetics vol. 42 pp. 19-27.*
GenBank Accession AF017328 GI 2394359 Sep. 19, 2007.*
GenBank Accession AF017328 GI: 2394359 Sep. 16, 1997.*
GenBank Accession U76395 GI 1667501 Dec. 21, 1996.*
Adams, E.J., et al., "Three new HLA-B alleles found in Mexican-Americans," *Tissue Angens*, Nov. 1995; 46(5): 414-16.
Belich, M.P. et al., "Unusual HLA-B alleles in two tribes of Brazilian Indians," *Nature*, May 28, 1992; 357(6376):326-9.
Bodmer, J.G. et al., "Nomenclature for factors of the HLA system, 1991," *Tissue Antigens*, vol. 39:161-173 (1992).
Bronson, S.K. et al., "Isolation and characterization of yeast artificial chromosome clones linking the HLA-B and HLA-C loci," *Proc. Natl. Acad. Sci. U.S.A.*, Mar. 1, 1991; 88(5):1676-80.
Cereb, Nezih et al., "Locus-specific conservation of the HLA class 1 introns by intra-locus homogenization," *Immunogenetics*, vol. 47:30-36 (1997).
Cereb, N. et al., "Nucleotide sequences of MHC class 1 introns 1, 2, and 3 in humans and intron 2 in nonhuman primates," *Tissue Antigens*, vol. 47:498-511 (1996).
Dominguez, O. et al., "Molecular typing of HLA-B27 alleles," *Immunogenetics*, vol. 36:277-282 (1992).

(Continued)

*Primary Examiner* — Amanda Haney
(74) *Attorney, Agent, or Firm* — Nixon & Vanderhye P.C.

(57) ABSTRACT

The present invention relates to the typing of HLA alleles. The sequence of exon 2 and exon 3 of the alleles HLA-B*3913, HLA-B*1406 and HLA-B*51new and of exon 2 of the alleles HLA-DRB1*0820, HLA-DRB1*04new and HLA-DRB4*01new are disclosed. The present invention relates to methods for typing of the alleles HLA-B*3913, HLA-B*1406 and HLA-B*51new. The present invention further provides primers and probes to be used in the methods for typing. A diagnostic kit comprising these primers and probes is also part of the present invention.

5 Claims, 6 Drawing Sheets

OTHER PUBLICATIONS

Figure 1:
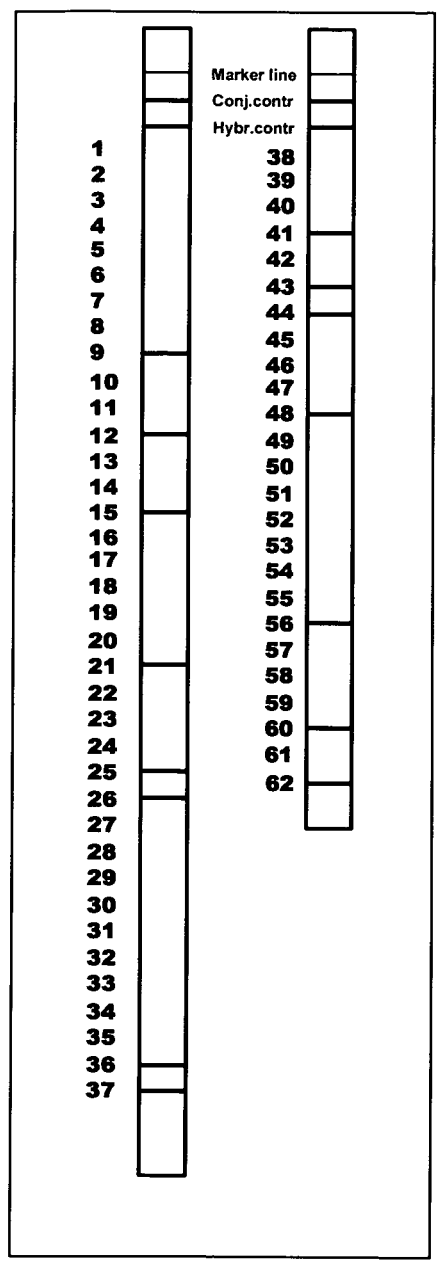

Ennis, P.D. et al., "Rapid cloning of HLA-A, B cDNA by using the polymerase chain reaction; frequency and nature of errors produced in amplification," *Proc. Natl. Acad. Sci. U.S.A.*, Apr. 1990;87(7):2833-7.

Erlich, H et al., HLA-DR, DQ and DP typing using PCR amplification and immobilized probes. 1991. European Journal lmmunogenetics. vol. 18. pp. 33-55.

Fernandez-Viña, Marcelo A. et al., "DNA Typing for HLA Class I Alleles: I. Subsets of HLA-A2 and of—A28," *Human Immunology*, vol. 33:163-173 (1992).

Fleischhauer, Katharina et al., "Bone Marrow-Allograft Rejection by T. Lymphocytes Recognizing a Single Amino Acid Difference in HLA-B44," *The New England Journal of Medicine*, vol. 323(26):1818-1822 (1990).

Genbank Accession U76395 GI 1667501 Pri Dec. 21, 1996.

Genbank Accession AF017328 GI 2394359 Pri Sep. 16, 1997.

Genbank Accession No. L12944 for Human MHC HLA-DR4-Dw4 cell surface glycoprotein.

Genbank Accession No. K02775 for Human MHC class II HLA-DR-beta (MT3) DNA, beta-1 exon.

Genbank Accession No. U88135 for Human MHC class II antigen (HLA-DR) gene, allele DRB1*08043, complete cds.

Gorski, J. et al., "Structural comparison of the genes of two HLA-DR supertypic groups: the loci encoding DRw52 and DRw53 are not truly allelic," *Immunogenetics*, 1987;25(6):397-402.

Hill, Adrian V.S. et al., "HLA class I typing by PCR:HLA-B27 and an African B27 subtype," *The Lancet*, vol. 337:640-642 (1991).

Kato, N. et al., "Molecular analysis of HLA-B39 subtypes," *Immunogenetics*, 1993;37(3):212-6.

Kawasaki, Ernest et al. "[27] Genetic Analysis Using Polymerase Chain Reaction—Amplified DNA and Immobilized Oligonucleotide Probes: Reverse Dot-Blot Typing," Methods in Enzymology, vol. 218:369-381(1993).

Kotsch, K et al. "Sequencing of HLA class I genes based on the conserved diversity of the noncoding regions: sequencing-based typing of the HLA-A gene," Tissue Antigens, vol. 50:178-191 (1997).

Mach, B. et al., "Genotypic typing of HLA class II: from the bench to the bedside," *Hum. Immunol.*, Apr. 1991;30(4):278-84.

Marsh, S.G.E., "HLA class II region sequences, 1998," *Tissue Antigens*, Apr. 1998;51(4 Pt 2):467-507.

Mersch et al. Homo Sapiens HLA-DRB1 gene, exon 2. Genbank Accession No. AJ000927 Jan. 1999.

Sanger, F. et al., "DNA sequencing with chain-terminating inhibitors," *Proc. Natl. Acad. Sci. U.S.A.*, vol. 74(12): 5463-5467 (1977).

Santamaria, P. et al., "Detection of novel sequence heterogeneity and haplotypic diversity of HLA class II genes," *Immunogenetics*, 1991;33(5-6):374-87.

Scheltinga, Sitha A. et al., "A Generic Sequencing Based typing approach for the identification of HLA—A Diversity," Human Immunology, vol. 57:120-128 (1997).

Spies, T. et al., "Structural organization of the DR subregion of the human major histocompatibility complex," *Proc. Natl. Acad. Sci. U.S.A.*, Aug. 1985;82(15):5165-9.

Summers, Colin W. et al., "Polymerase Chain Reaction Analysis of Transcriptional Patters of Expression of Class I HLA Genes," *Human Immunology*, vol. 32:176-182 (1991).

Tiercy, J.M. et al., "A new approach for the analysis of HLA class II polymorphism: 'HLA oligotyping'," *Blood Rev.*, Mar. 1990;4(1):9-15.

Watkins, D.I. et al., "New recombinant HLA-B alleles in a tribe of South American Amerindians indicate rapid evolution of MHC class I loci," *Nature*, May 28, 1992;357(6376):329-33.

Yoshida, Masayuki et al., "Polymerase-Chain-Reaction-Based Analysis of Polymorphism in the HLA-B Gene,"*Human Immunology*, vol. 34:257-266 (1992).

Zemmour, J. et al., "HLA Class I nucleotide sequences, 1992," *Tissue Antigens*, vol. 40:221-228 (1992).

De Canck, I. 1998 NCBI GI 3805792 Direct Submission.

Gomez-Casado, "Generation of the HLA B35, -B5, B-16, and B15 groups of alleles studied by intron 1 and 2 sequence analysis," *Immunogenetics*, 16: 469-476.

Gen Bank Accession No. M16731 for Human MHC class II HLA-DR4 1 first domain coding region for DR-beta chain mRNA (Dw4).

\* cited by examiner

SEQUENCE LISTING

<160> NUMBER OF SEQ ID NOS: 107

<210> SEQ ID NO 1
<211> LENGTH: 269

```
<212> TYPE: DNA
<213> ORGANISM: Homo sapiens

<400> SEQUENCE: 1
cacgtttctt ggagtactct acgtctgagt gtcatttctt caatgggacg gagcgggtgc    60
ggttcctgga cagatacttc tataaccaag aggagtacgt gcgcttcgac agcgacgtgg   120
gggagtaccg ggcggtgacg gagctggggc ggcctgatgc cgagtactgg aacagccaga   180
aggacttcct ggaagacagg cgggccctgg tggacaccta ctgcagacac aactacgggg   240
ttgtggagag cttcacagtg cagcggcga                                     269

<210> SEQ ID NO 2
<211> LENGTH: 89
<212> TYPE: PRT
<213> ORGANISM: Homo sapiens

<400> SEQUENCE: 2

Arg Phe Leu Glu Tyr Ser Thr Ser Glu Cys His Phe Phe Asn Gly Thr
  1               5                  10                  15

Glu Arg Val Arg Phe Leu Asp Arg Tyr Phe Tyr Asn Gln Glu Glu Tyr
             20                  25                  30

Val Arg Phe Asp Ser Asp Val Gly Glu Tyr Arg Ala Val Thr Glu Leu
         35                  40                  45

Gly Arg Pro Asp Ala Glu Tyr Trp Asn Ser Gln Lys Asp Phe Leu Glu
     50                  55                  60

Asp Arg Arg Ala Leu Val Asp Thr Tyr Cys Arg His Asn Tyr Gly Val
 65                  70                  75                  80

Val Glu Ser Phe Thr Val Gln Arg Arg
                 85

<210> SEQ ID NO 3
<211> LENGTH: 24
<212> TYPE: DNA
<213> ORGANISM: Homo sapiens

<400> SEQUENCE: 3
gatccttcgt gtccccacag cacg                                           24

<210> SEQ ID NO 4
<211> LENGTH: 27
<212> TYPE: DNA
<213> ORGANISM: Homo sapiens

<400> SEQUENCE: 4
ccccacagca cgtttcttgg agtactc                                        27

<210> SEQ ID NO 5
<211> LENGTH: 24
<212> TYPE: DNA
<213> ORGANISM: Homo sapiens

<400> SEQUENCE: 5
tgtccccaca gcacgtttct tgtg                                           24

<210> SEQ ID NO 6
<211> LENGTH: 20
<212> TYPE: DNA
<213> ORGANISM: Homo sapiens

<400> SEQUENCE: 6
tttcttggag caggttaaac                                                20
```

<210> SEQ ID NO 7
<211> LENGTH: 25
<212> TYPE: DNA
<213> ORGANISM: Homo sapiens

<400> SEQUENCE: 7
cacgtttctt gaagcaggat aagtt        25

<210> SEQ ID NO 8
<211> LENGTH: 20
<212> TYPE: DNA
<213> ORGANISM: Homo sapiens

<400> SEQUENCE: 8
cacagcacgt ttcttggagg        20

<210> SEQ ID NO 9
<211> LENGTH: 18
<212> TYPE: DNA
<213> ORGANISM: Homo sapiens

<400> SEQUENCE: 9
ctgtggcagc ctaagagg        18

<210> SEQ ID NO 10
<211> LENGTH: 22
<212> TYPE: DNA
<213> ORGANISM: Homo sapiens

<400> SEQUENCE: 10
tcgccgctgc actgtgaagc tc        22

<210> SEQ ID NO 11
<211> LENGTH: 16
<212> TYPE: DNA
<213> ORGANISM: Homo sapiens

<400> SEQUENCE: 11
attcccgcgc cgcgct        16

<210> SEQ ID NO 12
<211> LENGTH: 20
<212> TYPE: DNA
<213> ORGANISM: Homo sapiens

<400> SEQUENCE: 12
ctgcactgtg aagctctcca        20

<210> SEQ ID NO 13
<211> LENGTH: 18
<212> TYPE: DNA
<213> ORGANISM: Homo sapiens

<400> SEQUENCE: 13
gtactctacg tctgagtg        18

<210> SEQ ID NO 14
<211> LENGTH: 19
<212> TYPE: DNA
<213> ORGANISM: Homo sapiens

<400> SEQUENCE: 14
gcctgatgcc gagtactgg        19

```
<210> SEQ ID NO 15
<211> LENGTH: 19
<212> TYPE: DNA
<213> ORGANISM: Homo sapiens

<400> SEQUENCE: 15
agaaggactt cctggaaga                                              19

<210> SEQ ID NO 16
<211> LENGTH: 21
<212> TYPE: DNA
<213> ORGANISM: Homo sapiens

<400> SEQUENCE: 16
agccaggcgg gccctggtgg a                                           21

<210> SEQ ID NO 17
<211> LENGTH: 15
<212> TYPE: DNA
<213> ORGANISM: Homo sapiens

<400> SEQUENCE: 17
ggggttgtgg agagc                                                  15

<210> SEQ ID NO 18
<211> LENGTH: 18
<212> TYPE: DNA
<213> ORGANISM: Homo sapiens

<400> SEQUENCE: 18
ttcttcaatg ggacggag                                               18

<210> SEQ ID NO 19
<211> LENGTH: 18
<212> TYPE: DNA
<213> ORGANISM: Homo sapiens

<400> SEQUENCE: 19
ttcctggaca gatacttc                                               18

<210> SEQ ID NO 20
<211> LENGTH: 18
<212> TYPE: DNA
<213> ORGANISM: Homo sapiens

<400> SEQUENCE: 20
caagaggagt acgtgcgc                                               18

<210> SEQ ID NO 21
<211> LENGTH: 18
<212> TYPE: DNA
<213> ORGANISM: Homo sapiens

<400> SEQUENCE: 21
ggggagtacc gggcggtg                                               18

<210> SEQ ID NO 22
<211> LENGTH: 270
<212> TYPE: DNA
<213> ORGANISM: Homo sapiens

<400> SEQUENCE: 22
gctcccactc catgaggtat ttctacacct ccgtgtcccg gcccggccgc ggggagcccc    60
```

-continued

```
gcttcatctc agtgggctac gtggacgaca cgcagttcgt gaggttcgac agcgacgccg    120
cgagtccgag agaggagccg cgggcgccgt ggatagagca ggaggggccg gagtattggg    180
accgggagac acagatctcc aagaccaaca cacagactta ccgagagagc ctgcggaacc    240
tgcgcggcta ctacaaccag agcgaggccg                                     270
```

<210> SEQ ID NO 23
<211> LENGTH: 276
<212> TYPE: DNA
<213> ORGANISM: Homo sapiens

<400> SEQUENCE: 23

```
ggtctcacac cctccagagg atgtacggct gcgacgtggg gccggacggg cgcctcctcc     60
gcgggcataa ccagttcgcc tacgacggca aggattacat cgccctgaac gaggacctga    120
gctcctggac cgcggcggac accgcggctc agatcaccca gcgcaagtgg gaggcggccc    180
gtgtggcgga gcagctgaga acctacctgg agggcacgtg cgtggagtgg ctccgcagat    240
acctggagaa cgggaaggag acgctgcagc gcgcgg                              276
```

<210> SEQ ID NO 24
<211> LENGTH: 90
<212> TYPE: PRT
<213> ORGANISM: Homo sapiens

<400> SEQUENCE: 24

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80

Leu Arg Gly Tyr Tyr Asn Gln Ser Glu Ala
                85                  90

<210> SEQ ID NO 25
<211> LENGTH: 92
<212> TYPE: PRT
<213> ORGANISM: Homo sapiens

<400> SEQUENCE: 25

Gly Ser His Thr Leu Gln Arg Met Tyr Gly Cys Asp Val Gly Pro Asp
1               5                   10                  15

Gly Arg Leu Leu Arg Gly His Asn Gln Phe Ala Tyr Asp Gly Lys Asp
            20                  25                  30

Tyr Ile Ala Leu Asn Glu Asp Leu Ser Ser Trp Thr Ala Ala Asp Thr
        35                  40                  45

Ala Ala Gln Ile Thr Gln Arg Lys Trp Glu Ala Ala Arg Val Ala Glu
    50                  55                  60

Gln Leu Arg Thr Tyr Leu Glu Gly Thr Cys Val Glu Trp Leu Arg Arg
65                  70                  75                  80

Tyr Leu Glu Asn Gly Lys Glu Thr Leu Gln Arg Ala
                85                  90

```
<210> SEQ ID NO 26
<211> LENGTH: 22
<212> TYPE: DNA
<213> ORGANISM: Homo sapiens

<400> SEQUENCE: 26
gggaggagcg aggggaccsc ac                                              22

<210> SEQ ID NO 27
<211> LENGTH: 23
<212> TYPE: DNA
<213> ORGANISM: Homo sapiens

<400> SEQUENCE: 27
ggaggccatc cccggcgacc tat                                             23

<210> SEQ ID NO 28
<211> LENGTH: 18
<212> TYPE: DNA
<213> ORGANISM: Homo sapiens

<400> SEQUENCE: 28
gggacacgga ggtgtaga                                                   18

<210> SEQ ID NO 29
<211> LENGTH: 16
<212> TYPE: DNA
<213> ORGANISM: Homo sapiens

<400> SEQUENCE: 29
ccggcccggc cgcggg                                                     16

<210> SEQ ID NO 30
<211> LENGTH: 18
<212> TYPE: DNA
<213> ORGANISM: Homo sapiens

<400> SEQUENCE: 30
gcttcatctc agtgggct                                                   18

<210> SEQ ID NO 31
<211> LENGTH: 17
<212> TYPE: DNA
<213> ORGANISM: Homo sapiens

<400> SEQUENCE: 31
gttcgtgagg ttcgaca                                                    17

<210> SEQ ID NO 32
<211> LENGTH: 19
<212> TYPE: DNA
<213> ORGANISM: Homo sapiens

<400> SEQUENCE: 32
gagtccgaga gaggagccg                                                  19

<210> SEQ ID NO 33
<211> LENGTH: 17
<212> TYPE: DNA
<213> ORGANISM: Homo sapiens

<400> SEQUENCE: 33
ggccggagta ttgggac                                                    17
```

```
<210> SEQ ID NO 34
<211> LENGTH: 18
<212> TYPE: DNA
<213> ORGANISM: Homo sapiens

<400> SEQUENCE: 34
ggaccgggag acacagat                                                 18

<210> SEQ ID NO 35
<211> LENGTH: 17
<212> TYPE: DNA
<213> ORGANISM: Homo sapiens

<400> SEQUENCE: 35
agatctccaa gaccaac                                                  17

<210> SEQ ID NO 36
<211> LENGTH: 17
<212> TYPE: DNA
<213> ORGANISM: Homo sapiens

<400> SEQUENCE: 36
cacagactta ccgagag                                                  17

<210> SEQ ID NO 37
<211> LENGTH: 17
<212> TYPE: DNA
<213> ORGANISM: Homo sapiens

<400> SEQUENCE: 37
accgagagag cctgcgg                                                  17

<210> SEQ ID NO 38
<211> LENGTH: 17
<212> TYPE: DNA
<213> ORGANISM: Homo sapiens

<400> SEQUENCE: 38
cggaacctgc gcggcta                                                  17

<210> SEQ ID NO 39
<211> LENGTH: 17
<212> TYPE: DNA
<213> ORGANISM: Homo sapiens

<400> SEQUENCE: 39
agaggatgta cggctgc                                                  17

<210> SEQ ID NO 40
<211> LENGTH: 16
<212> TYPE: DNA
<213> ORGANISM: Homo sapiens

<400> SEQUENCE: 40
gacgtggggc cggacg                                                   16

<210> SEQ ID NO 41
<211> LENGTH: 17
<212> TYPE: DNA
<213> ORGANISM: Homo sapiens

<400> SEQUENCE: 41
gacgggcgcc tcctccg                                                  17
```

```
<210> SEQ ID NO 42
<211> LENGTH: 20
<212> TYPE: DNA
<213> ORGANISM: Homo sapiens

<400> SEQUENCE: 42
tcctccgcgg gcataaccag                                              20

<210> SEQ ID NO 43
<211> LENGTH: 19
<212> TYPE: DNA
<213> ORGANISM: Homo sapiens

<400> SEQUENCE: 43
gggcataacc agttcgcct                                               19

<210> SEQ ID NO 44
<211> LENGTH: 18
<212> TYPE: DNA
<213> ORGANISM: Homo sapiens

<400> SEQUENCE: 44
gaggacctga gctcctgg                                                18

<210> SEQ ID NO 45
<211> LENGTH: 17
<212> TYPE: DNA
<213> ORGANISM: Homo sapiens

<400> SEQUENCE: 45
cggcccgtgt ggcggag                                                 17

<210> SEQ ID NO 46
<211> LENGTH: 18
<212> TYPE: DNA
<213> ORGANISM: Homo sapiens

<400> SEQUENCE: 46
gcagctgaga acctacct                                                18

<210> SEQ ID NO 47
<211> LENGTH: 17
<212> TYPE: DNA
<213> ORGANISM: Homo sapiens

<400> SEQUENCE: 47
tggagggcac gtgcgtg                                                 17

<210> SEQ ID NO 48
<211> LENGTH: 16
<212> TYPE: DNA
<213> ORGANISM: Homo sapiens

<400> SEQUENCE: 48
cgtggagtgg ctccgc                                                  16

<210> SEQ ID NO 49
<211> LENGTH: 18
<212> TYPE: DNA
<213> ORGANISM: Homo sapiens

<400> SEQUENCE: 49
tccgcagata cctggaga                                                18
```

```
<210> SEQ ID NO 50
<211> LENGTH: 243
<212> TYPE: DNA
<213> ORGANISM: Homo sapiens

<400> SEQUENCE: 50
tttcttggag caggttaaac ctgagtgtca tttcttcaac gggacggagc gggtgcggtt        60
cctggacaga tacttctatc accaagagga gtacgtgcgc ttcgacagcg acgtggggga      120
gtaccgggcg gtgacggagc tggggcggcc tgatgccgag tactggaaca gccagaagga      180
cctcctggag cagaagcggg ccgcggtgga cacctactgc agacacaact acggggttgg      240
tga                                                                    243

<210> SEQ ID NO 51
<211> LENGTH: 80
<212> TYPE: PRT
<213> ORGANISM: Homo sapiens

<400> SEQUENCE: 51

Phe Leu Glu Gln Val Lys Pro Glu Cys His Phe Phe Asn Gly Thr Glu
 1               5                  10                  15

Arg Val Arg Phe Leu Asp Arg Tyr Phe Tyr His Gln Glu Glu Tyr Val
            20                  25                  30

Arg Phe Asp Ser Asp Val Gly Glu Tyr Arg Ala Val Thr Glu Leu Gly
        35                  40                  45

Arg Pro Asp Ala Glu Tyr Trp Asn Ser Gln Lys Asp Leu Leu Glu Gln
    50                  55                  60

Lys Arg Ala Ala Val Asp Thr Tyr Cys Arg His Asn Tyr Gly Val Gly
65                  70                  75                  80

<210> SEQ ID NO 52
<211> LENGTH: 23
<212> TYPE: DNA
<213> ORGANISM: Homo sapiens

<400> SEQUENCE: 52
acgtttcttg gagcaggtta aac                                               23

<210> SEQ ID NO 53
<211> LENGTH: 24
<212> TYPE: DNA
<213> ORGANISM: Homo sapiens

<400> SEQUENCE: 53
accggatcct tcgtgtcccc acag                                              24

<210> SEQ ID NO 54
<211> LENGTH: 19
<212> TYPE: DNA
<213> ORGANISM: Homo sapiens

<400> SEQUENCE: 54
taagtgtgag tgtcatttc                                                    19

<210> SEQ ID NO 55
<211> LENGTH: 15
<212> TYPE: DNA
<213> ORGANISM: Homo sapiens

<400> SEQUENCE: 55
cagaagcggg ccgcg                                                        15
```

```
<210> SEQ ID NO 56
<211> LENGTH: 20
<212> TYPE: DNA
<213> ORGANISM: Homo sapiens

<400> SEQUENCE: 56
atcaccaaga ggagtacgtg                                               20

<210> SEQ ID NO 57
<211> LENGTH: 20
<212> TYPE: DNA
<213> ORGANISM: Homo sapiens

<400> SEQUENCE: 57
cacaactacg gggttggtga                                               20

<210> SEQ ID NO 58
<211> LENGTH: 19
<212> TYPE: DNA
<213> ORGANISM: Homo sapiens

<400> SEQUENCE: 58
gcctgatgcc gagtactgg                                                19

<210> SEQ ID NO 59
<211> LENGTH: 15
<212> TYPE: DNA
<213> ORGANISM: Homo sapiens

<400> SEQUENCE: 59
gccgcggtgg acacc                                                    15

<210> SEQ ID NO 60
<211> LENGTH: 18
<212> TYPE: DNA
<213> ORGANISM: Homo sapiens

<400> SEQUENCE: 60
ccagaaggac ctcctgga                                                 18

<210> SEQ ID NO 61
<211> LENGTH: 21
<212> TYPE: DNA
<213> ORGANISM: Homo sapiens

<400> SEQUENCE: 61
cagatacttc tatcaccaag a                                             21

<210> SEQ ID NO 62
<211> LENGTH: 15
<212> TYPE: DNA
<213> ORGANISM: Homo sapiens

<400> SEQUENCE: 62
gggccgaggt ggaca                                                    15

<210> SEQ ID NO 63
<211> LENGTH: 18
<212> TYPE: DNA
<213> ORGANISM: Homo sapiens

<400> SEQUENCE: 63
ccagaaggac ctcctgga                                                 18
```

```
<210> SEQ ID NO 64
<211> LENGTH: 15
<212> TYPE: DNA
<213> ORGANISM: Homo sapiens

<400> SEQUENCE: 64
ggggttgtgg agagc                                                        15

<210> SEQ ID NO 65
<211> LENGTH: 16
<212> TYPE: DNA
<213> ORGANISM: Homo sapiens

<400> SEQUENCE: 65
gaggagtacg cgcgct                                                       16

<210> SEQ ID NO 66
<211> LENGTH: 16
<212> TYPE: DNA
<213> ORGANISM: Homo sapiens

<400> SEQUENCE: 66
gagcgagtgt ggaacc                                                       16

<210> SEQ ID NO 67
<211> LENGTH: 270
<212> TYPE: DNA
<213> ORGANISM: Homo sapiens

<400> SEQUENCE: 67
cacgtttctt ggagcaggct aagtgtgagt gtcatttcct caatgggacg gagcgagtgt       60
ggaacctgat cagatacatc tataaccaag aggagtacgc gcgctacaac agtgatctgg      120
gggagtacca gcggtgacg gagctggggc ggcctgacgc tgagtactgg aacagccaga       180
aggacctcct ggagcggagg cgggccgagg tggacaccta ctgcagatac aactacgggg      240
ttgtggagag cttcacagtg cagcggcgag                                       270

<210> SEQ ID NO 68
<211> LENGTH: 289
<212> TYPE: DNA
<213> ORGANISM: Homo sapiens

<400> SEQUENCE: 68
gatccttcgt gtccccacag cacgtttctt ggagcaggtt aaacctgagt gtcatttctt       60
caacgggacg gagcgggtgc ggttcctgga cagatacttc tatcaccaag aggagtacgt      120
gcgcttcgac agcgacgtgg gggagtaccg gcggtgacg gagctggggc ggcctgatgc       180
cgagtactgg aacagccaga aggacctcct ggagcagaag cgggccgcgg tggacaccta      240
ctgcagacac aactacgggg ttggtgagag cttcacagtg cagcggcga                  289

<210> SEQ ID NO 69
<211> LENGTH: 268
<212> TYPE: DNA
<213> ORGANISM: Homo sapiens

<400> SEQUENCE: 69
acgtttcttg gagcaggtta aacctgagtg tcatttcttc aacgggacgg agcgggtgcg       60
gttcctggac agatacttct atcaccaaga ggagtacgtg cgcttcgaca gcgacgtggg      120
ggagtaccgg gcggtgacgg agctggggcg gcctgatgcc gagtactgga acagccagaa      180
```

```
ggacctcctg agcagaagc gggccgcggt ggacacctac tgcagacaca actacggggt        240
tggtgagagc ttcacagtgc agcggcga                                          268

<210> SEQ ID NO 70
<211> LENGTH: 315
<212> TYPE: DNA
<213> ORGANISM: Homo sapiens

<400> SEQUENCE: 70
accggatcct tcgtgtcccc acagcacgtt tcttggagca ggctaagtgt gagtgtcatt        60
tcctcaatgg gacggagcga gtgtggaacc tgatcagata catctataac caagaggagt       120
acgcgcgcta caacagtgat ctgggggagt accaggcggt gacggagctg ggcggcctg        180 acgctgagta ctggaacagc cagaaggacc tcctggagcg gaggcgggcc gaggtggaca       240
cctactgcag atacaactac ggggttgtgg agagcttcac agtgcagcgg cgaggtgagc       300
atggtggagg gcggg                                                        315

<210> SEQ ID NO 71
<211> LENGTH: 249
<212> TYPE: DNA
<213> ORGANISM: Homo sapiens

<400> SEQUENCE: 71
taagtgtgag tgtcatttcc tcaatgggac ggagcgagtg tggaacctga tcagatacat        60
ctataaccaa gaggagtacg cgcgctacaa cagtgatctg ggggagtacc aggcggtgac       120
ggagctgggg cggcctgacg ctgagtactg gaacagccag aaggacctcc tggagcggag       180
gcgggccgag gtggacacct actgcagatc aactacgggg ttgtggagag cttcacagtg       240
cagcggcga                                                               249

<210> SEQ ID NO 72
<211> LENGTH: 270
<212> TYPE: DNA
<213> ORGANISM: Homo sapiens

<400> SEQUENCE: 72
gctcccactc catgaggtat ttctacaccg ccgtgtcccg gcccggccgc ggggagcccc        60
gcttcatctc agtgggctac gtggacgaca cgcagttcgt gaggttcgac agcgacgccg       120
cgagtccgag agaggagccg cgggcgccgt ggatagagca ggaggggccg gaatattggg       180
accggaacac acagatctgc aagaccaaca cacagactga ccgagagagc ctgcggaacc       240
tgcgcggcta ctacaaccag agcgaggccg                                        270

<210> SEQ ID NO 73
<211> LENGTH: 276
<212> TYPE: DNA
<213> ORGANISM: Homo sapiens

<400> SEQUENCE: 73
ggtctcacac cctccagagg atgtacggct gcgacgtggg gccggacggg cgcctcctcc        60
gcgggtataa ccagttcgcc tacgacggca aggattacat cgccctgaac gaggacctga       120
gctcctggac cgcggcggac accgcggctc agatcaccca gcgcaagtgg gaggcggccc       180
gtgaggcgga gcagctgaga gcctacctgg agggcacgtg cgtggagtgg ctccgcagac       240
acctggagaa cgggaaggag acgctgcagc gcgcgg                                 276

<210> SEQ ID NO 74
```

<211> LENGTH: 270
<212> TYPE: DNA
<213> ORGANISM: Homo sapiens

<400> SEQUENCE: 74

```
gctcccactc catgaggtat ttctacaccg ccatgtcccg gcccggccgc ggggagcccc    60
gcttcattgc agtgggctac gtggacgaca cccagttcgt gaggttcgac agcgacgccg   120
cgagtccgag gacggagccc cgggcgccat ggatagagca ggaggggccg gagtattggg   180
accggaacac acagatcttc aagaccaaca cacagactta ccgagagaac ctgcggatcg   240
cgctccgcta ctacaaccag agcgaggccg                                    270
```

<210> SEQ ID NO 75
<211> LENGTH: 276
<212> TYPE: DNA
<213> ORGANISM: Homo sapiens

<400> SEQUENCE: 75

```
ggtctcacac ttggcagacg atgtatggct gcgacgtggg gccggacggg cgcctcctcc    60
ccgggcataa ccagtacgcc tacgacggca aagattacat cgccctgaac gaggacctga   120
gctcctggac cgcggcggac accgcggctc agatcaccca gcgcaagtgg gaggcggccc   180
gtgaggcgga gcagctgaga gcctacctgg agggcctgtg cgtggagtgg ctccgcagac   240
acctggagaa cgggaaggag tcgctgcagc gcgcgg                             276
```

<210> SEQ ID NO 76
<211> LENGTH: 17
<212> TYPE: DNA
<213> ORGANISM: Homo sapiens

<400> SEQUENCE: 76

```
tctacaccgc cgtgtcc                                                   17
```

<210> SEQ ID NO 77
<211> LENGTH: 18
<212> TYPE: DNA
<213> ORGANISM: Homo sapiens

<400> SEQUENCE: 77

```
gcgacgccgc gagtccga                                                  18
```

<210> SEQ ID NO 78
<211> LENGTH: 17
<212> TYPE: DNA
<213> ORGANISM: Homo sapiens

<400> SEQUENCE: 78

```
ggccggaata ttgggac                                                   17
```

<210> SEQ ID NO 79
<211> LENGTH: 16
<212> TYPE: DNA
<213> ORGANISM: Homo sapiens

<400> SEQUENCE: 79

```
ggaccggaac acacag                                                    16
```

<210> SEQ ID NO 80
<211> LENGTH: 17
<212> TYPE: DNA
<213> ORGANISM: Homo sapiens

```
<400> SEQUENCE: 80
acagatctgc aagacca                                                    17

<210> SEQ ID NO 81
<211> LENGTH: 16
<212> TYPE: DNA
<213> ORGANISM: Homo sapiens

<400> SEQUENCE: 81
acagactgac cgagag                                                     16

<210> SEQ ID NO 82
<211> LENGTH: 19
<212> TYPE: DNA
<213> ORGANISM: Homo sapiens

<400> SEQUENCE: 82
ggaacctgcg cggctacta                                                  19

<210> SEQ ID NO 83
<211> LENGTH: 16
<212> TYPE: DNA
<213> ORGANISM: Homo sapiens

<400> SEQUENCE: 83
agaggatgta cggctg                                                     16

<210> SEQ ID NO 84
<211> LENGTH: 17
<212> TYPE: DNA
<213> ORGANISM: Homo sapiens

<400> SEQUENCE: 84
cgacgtgggg ccggacg                                                    17

<210> SEQ ID NO 85
<211> LENGTH: 19
<212> TYPE: DNA
<213> ORGANISM: Homo sapiens

<400> SEQUENCE: 85
gggtataacc agttcgcct                                                  19

<210> SEQ ID NO 86
<211> LENGTH: 17
<212> TYPE: DNA
<213> ORGANISM: Homo sapiens

<400> SEQUENCE: 86
aggacctgag ctcctgg                                                    17

<210> SEQ ID NO 87
<211> LENGTH: 16
<212> TYPE: DNA
<213> ORGANISM: Homo sapiens

<400> SEQUENCE: 87
gcccgtgagg cggagc                                                     16

<210> SEQ ID NO 88
<211> LENGTH: 18
<212> TYPE: DNA
<213> ORGANISM: Homo sapiens
```

```
<400> SEQUENCE: 88
gcagctgaga gcctacct                                          18

<210> SEQ ID NO 89
<211> LENGTH: 17
<212> TYPE: DNA
<213> ORGANISM: Homo sapiens

<400> SEQUENCE: 89
ccgcagacac ctggaga                                           17

<210> SEQ ID NO 90
<211> LENGTH: 18
<212> TYPE: DNA
<213> ORGANISM: Homo sapiens

<400> SEQUENCE: 90
gcttcattgc agtgggct                                          18

<210> SEQ ID NO 91
<211> LENGTH: 23
<212> TYPE: DNA
<213> ORGANISM: Homo sapiens

<400> SEQUENCE: 91
cgagtccgag gacggagccc cgg                                    23

<210> SEQ ID NO 92
<211> LENGTH: 18
<212> TYPE: DNA
<213> ORGANISM: Homo sapiens

<400> SEQUENCE: 92
cagatcttca agaccaac                                          18

<210> SEQ ID NO 93
<211> LENGTH: 19
<212> TYPE: DNA
<213> ORGANISM: Homo sapiens

<400> SEQUENCE: 93
cacacagact taccgagag                                         19

<210> SEQ ID NO 94
<211> LENGTH: 18
<212> TYPE: DNA
<213> ORGANISM: Homo sapiens

<400> SEQUENCE: 94
cgagagaacc tgcggatc                                          18

<210> SEQ ID NO 95
<211> LENGTH: 17
<212> TYPE: DNA
<213> ORGANISM: Homo sapiens

<400> SEQUENCE: 95
cggatcgcgc tccgcta                                           17

<210> SEQ ID NO 96
<211> LENGTH: 17
<212> TYPE: DNA
<213> ORGANISM: Homo sapiens
```

```
<400> SEQUENCE: 96
tctacaccgc catgtcc                                               17

<210> SEQ ID NO 97
<211> LENGTH: 17
<212> TYPE: DNA
<213> ORGANISM: Homo sapiens

<400> SEQUENCE: 97
gcgacgccgc gagtccg                                               17

<210> SEQ ID NO 98
<211> LENGTH: 17
<212> TYPE: DNA
<213> ORGANISM: Homo sapiens

<400> SEQUENCE: 98
acacttggca gacgatg                                               17

<210> SEQ ID NO 99
<211> LENGTH: 16
<212> TYPE: DNA
<213> ORGANISM: Homo sapiens

<400> SEQUENCE: 99
ggagggcctg tgcgtg                                                16

<210> SEQ ID NO 100
<211> LENGTH: 19
<212> TYPE: DNA
<213> ORGANISM: Homo sapiens

<400> SEQUENCE: 100
cataaccagt acgcctacg                                             19

<210> SEQ ID NO 101
<211> LENGTH: 15
<212> TYPE: DNA
<213> ORGANISM: Homo sapiens

<400> SEQUENCE: 101
gtggagtggc tccgc                                                 15

<210> SEQ ID NO 102
<211> LENGTH: 16
<212> TYPE: DNA
<213> ORGANISM: Homo sapiens

<400> SEQUENCE: 102
gacgggcgcc tcctcc                                                16

<210> SEQ ID NO 103
<211> LENGTH: 90
<212> TYPE: PRT
<213> ORGANISM: Homo sapiens

<400> SEQUENCE: 103

Gly Ser His Ser Met Arg Tyr Ser Tyr Thr Ala Val Ser Arg Pro Gly
 1               5                  10                  15

Arg Gly Glu Pro Arg Phe Ile Ser Val Gly Tyr Val Asp Asp Thr Gln
                20                  25                  30

Phe Val Arg Phe Asp Ser Asp Ala Ala Ser Pro Arg Glu Glu Pro Arg
            35                  40                  45
```

-continued

```
Ala Pro Trp Ile Glu Gln Glu Gly Pro Glu Tyr Trp Asp Arg Asn Thr
             50                  55                  60
Gln Ile Cys Lys Thr Asn Thr Gln Thr Asp Arg Glu Ser Leu Arg Asn
 65                  70                  75                  80
Leu Arg Gly Tyr Tyr Asn Gln Ser Glu Ala
                 85                  90

<210> SEQ ID NO 104
<211> LENGTH: 92
<212> TYPE: PRT
<213> ORGANISM: Homo sapiens

<400> SEQUENCE: 104

Gly Ser His Thr Leu Gln Arg Met Tyr Gly Cys Asp Val Gly Pro Asp
  1               5                  10                  15
Gly Arg Leu Leu Arg Gly Tyr Asn Gln Phe Ala Tyr Asp Gly Lys Asp
                 20                  25                  30
Tyr Ile Ala Leu Asn Glu Asp Leu Ser Ser Trp Thr Ala Ala Asp Thr
             35                  40                  45
Ala Ala Gln Ile Thr Gln Arg Lys Trp Glu Ala Ala Arg Glu Ala Glu
         50                  55                  60
Gln Leu Arg Ala Tyr Leu Glu Gly Thr Cys Val Glu Trp Leu Arg Arg
 65                  70                  75                  80
His Leu Glu Asn Gly Lys Glu Thr Leu Gln Arg Ala
                 85                  90

<210> SEQ ID NO 105
<211> LENGTH: 90
<212> TYPE: PRT
<213> ORGANISM: Homo sapiens

<400> SEQUENCE: 105

Gly Ser His Ser Met Arg Tyr Phe Tyr Thr Ala Met Ser Arg Pro Gly
  1               5                  10                  15
Arg Gly Glu Pro Arg Phe Ile Ala Val Gly Tyr Val Asp Asp Thr Gln
                 20                  25                  30
Phe Val Arg Phe Asp Ser Asp Ala Ala Ser Pro Arg Thr Glu Pro Arg
             35                  40                  45
Ala Pro Trp Ile Glu Gln Glu Gly Pro Glu Tyr Trp Asp Arg Asn Thr
         50                  55                  60
Gln Ile Phe Lys Thr Asn Thr Gln Thr Tyr Arg Glu Asn Leu Arg Ile
 65                  70                  75                  80
Ala Leu Arg Tyr Tyr Asn Gln Ser Glu Ala
                 85                  90

<210> SEQ ID NO 106
<211> LENGTH: 92
<212> TYPE: PRT
<213> ORGANISM: Homo sapiens

<400> SEQUENCE: 106

Gly Ser His Thr Trp Gln Thr Met Tyr Gly Cys Asp Val Gly Pro Asp
  1               5                  10                  15
Gly Arg Leu Leu Pro Gly His Asn Gln Tyr Ala Tyr Asp Gly Lys Asp
                 20                  25                  30
Tyr Ile Ala Leu Asn Glu Asp Leu Ser Ser Trp Thr Ala Ala Asp Thr
             35                  40                  45
Ala Ala Gln Ile Thr Gln Arg Lys Trp Glu Ala Ala Arg Glu Ala Glu
```

```
               50                  55                  60
Gln Leu Arg Ala Tyr Leu Glu Gly Leu Cys Val Glu Trp Leu Arg Arg
 65                  70                  75                  80

His Leu Glu Asn Gly Lys Glu Ser Leu Gln Arg Ala
                 85                  90

<210> SEQ ID NO 107
<211> LENGTH: 21
<212> TYPE: DNA
<213> ORGANISM: Homo sapiens

<400> SEQUENCE: 107
cccgccctcc accatgctca c                                            21
```

METHOD FOR TYPING HLA ALLELES

This application is a divisional of application Ser. No. 10/334,488 filed Dec. 30, 2002, which is a divisional of application Ser. No. 09/673,809, filed Oct. 20, 2000, now U.S. Pat. No. 6,528,261, which claims priority to International Application No. PCT/EP99/02614, filed Apr. 19, 1999, and European Application No. 98870088.6, filed Apr. 20, 1998, all of which disclosures are incorporated herein by reference.

FIELD OF THE INVENTION

This invention relates to the typing of human leukocyte antigen (HLA) alleles. More particularly, the present invention relates to the typing of new HLA alleles.

BACKGROUND OF THE INVENTION

The human major histocompatibility complex (MHC) is contained within about 4 Mbp of DNA on the short arm of chromosome 6 at 6p21.3 (Campbell and Trowsdale, 1993). The human MHC is divided into class I, class II and class III regions. The genes of class I and class II encode highly polymorphic cell-surface molecules that bind and present processed antigens in the form of peptides to T-lymphocytes, initiating both cellular and humoral immune responses. The class I molecules, HLA-A, -B, and -C, are found on most nucleated cells. They are cell-surface glycoproteins that bind and present processed peptides derived from endogenously synthesized proteins to CD8+ T-cells. These heterodimers consist of an HLA-encoded α-chain associated with a non-MHC encoded monomorphic polypeptide, $β_2$-microglobulin (Townsend and Bodmer, 1989; Spencer and Parham, 1996). The class II molecules are encoded in the HLA-D region. These cell-surface glycoproteins consist of HLA-encoded α-, and β-chains, associated as heterodimers on the cell surface of antigen-presenting cells such as B-cells and macrophages. Class II molecules serve as receptors for processed peptides. However, these peptides are derived predominantly from membrane and extracellular proteins and are presented to CD4+ T-cells. The HLA-D region contains several class II genes and has three main subregions: HLA-DR, -DQ, and -DP. Both the HLA-DQ and -DP regions contain one functional gene for each of their α- and β-chains. The HLA-DR subregion contains one functional gene for the α-chain; the number of functional genes for the β-chain varies from one to two according to the haplotype (Andersson et al., 1987; Apple and Erlich, 1996).

A variety of techniques are currently used to detect HLA polymorphism, including serological, biochemical, T-cell recognition and, most recently, molecular biological methods.

Serology remains the mainstay method for HLA typing—especially for class I—for many routine histocompatibility laboratories. The micro-lymphocytotoxicity assay (Kissmeyer et al., 1969; Terasaki and McClelland, 1964) is the standard approach: viable peripheral blood mononuclear cells (class I) or separate B-cells (class II) are mixed with antisera (polyclonal or monoclonal) of known HLA specificity.

Detection of polymorphism can be achieved by looking at the different amino acid composition of HLA molecules through biochemical techniques such as one-dimensional isoelectric focusing (IEF; Yang, 1987). This method relies on amino acid substitutions contributing to changes in charge of the HLA molecule.

Another HLA typing method is the mixed lymphocyte reaction (MLR). Concurrent to observations being made using HLA-specific antisera, it was noted that lymphocytes from two unrelated sources, when mixed in culture, would proliferate (Hirschorn et al., 1963).

Analysis of HLA specificities from DNA provided a new approach to defining their polymorphic differences. Rather than looking at differences in the expressed molecule, polymorphism is characterized at the nucleotide level.

An important and powerful development in the field of molecular biology has been the polymerase chain reaction (PCR; Mullis et al., 1986; Mullis and Faloona, 1987). In tissue typing, PCR is used to amplify the polymorphic regions of HLA genes. This HLA PCR product can then be analysed for its polymorphic differences, to establish the tissue type. A number of such approaches have been developed, including hetero duplex analysis of PCR products (Clay et al., 1994), single-stranded conformational polymorphism analysis of the PCR product (PCR-SSCP; Yoshida et al., 1992), sequence-based typing (SBT; Santamaria et al., 1992 and 1993), the use of sequence specific primers in PCR reaction (PCR-SSP; Olerup and Zetterquist, 1991), the use of PCR in combination with sequence-specific oligonucleotide probing (PCR-SSOP; Saiki et al., 1986) or probing by reverse dot-blot (Saiki et al., 1989). These approaches, used singly or in combination, have all been applied as DNA-based methods for tissue-typing of class I and class II HLA specificities.

For class I alleles, hypervariable regions are found at different degrees in both exon 2 and exon 3, which encode the peptide binding groove of the class I molecule. Polymorphism within class II is contained mainly within defined hypervariable regions in exon 2. These polymorphisms make differentiation between alleles achievable through hybridization with relevant probes.

AIMS OF THE INVENTION

It is an aim of the present invention to provide a method for typing of the alleles HLA-DRB1*0820, HLA-DRB1*04new, HLA-DRB4*01new, HLA-B*3913, HLA-B*1406 and/or HLA-B*51new.

It is a more specific aim of the present invention to provide a method for typing of said alleles, with said method comprising an amplification step and a hybridization step.

It is also an aim of the present invention to provide primers for said amplification step.

It is also an aim of the present invention to provide probes for said hybridization step.

It is also an aim of the present invention to provide a diagnostic kit enabling said method for typing.

It is another aim of the present invention to provide a method for detection of the protein fragments encode by the HLA-DRB1*0820, HLA-DRB1*04new, HLA-DRB4*01new, HLA-B*3913, HLA-B*1406 and/or HLA-B*51new genes.

It is another aim of the present invention to provide an antiserum or a ligand for use in the detection of said protein fragments.

It is another aim of the present invention to provide a diagnostic kit for the detection of said protein fragment.

DETAILED DESCRIPTION OF THE INVENTION

The present invention discloses the sequence of exon 2 of the HLA allele DRB1*0820. This sequence is identified by SEQ ID NO 1 and is shown below.

```
                                                         (SEQ ID NO 1)
 5                    10                   15                  20      (47)
CA CGT TTC TTG GAG TAC TCT ACG TCT GAG TGT CAT TTC TTC AAT GGG 25                   30                  35      (92)
    ACG GAG CGG GTG CGG TTC CTG GAC AGA TAC TTC TAT AAC CAA GAG 40                   45                  50     (137)
    GAG TAC GTG CGC TTC GAC AGC GAC GTG GGG GAG TAC CGG GCG GTG 55                   60                  65     (182)
    ACG GAG CTG GGG CGG CCT GAT GCC GAG TAC TGG AAC AGC CAG AAG 70                   75                  80     (227)
    GAC TTC CTG GAA GAC AGG CGG GCC CTG GTG GAC ACC TAC TGC AGA 85                   90
    CAC AAC TAC GGG GTT GTG GAG AGC TTC ACA GTG CAG CGG CGA
```

The sequence is shown from 5' to 3' and runs from codon 5 to codon 94 of exon 2. The numbering of the codons is indicated. The nucleotide positions are indicated between brackets. This sequence has been submitted to the EMBL database and was assigned the accession number AJ000927.

The allele DRB1*0820 is a novel allele that has not been previously described.

The present invention also discloses the sequence of exon 2 of the HLA allele DRB1*04new. This sequence is identified by SEQ ID NO 50 and is shown below.

```
                                                        (SEQ ID NO 50)
   6                  10                   15                  20      (43)
   T TTC TTG GAG CAG GTT AAA CCT GAG TGT CAT TTC TTC AAC GGG 25                   30                  35      (88)
    ACG GAG CGG GTG CGG TTC CTG GAC AGA TAC TTC TAT CAC CAA GAG 40                   45                  50     (133)
    GAG TAC GTG CGC TTC GAC AGC GAC GTG GGG GAG TAC CGG GCG GTG 55                   60                  65     (178)
    ACG GAG CTG GGG CGG CCT GAT GCC GAG TAC TGG AAC AGC CAG AAG 70                   75                  80     (223)
    GAC CTC CTG GAG CAG AAG CGG GCC GCG GTG GAC ACC TAC TGC AGA

85
    CAC AAC TAC GGG GTT GGT GA
```

The sequence is shown from 5' to 3' and runs from codon 6 to codon 87 of exon 2. The numbering of the codons is indicated. The nucleotide positions are indicated between brackets.

This sequence has been submitted to the EMBL database and was assigned the accession number AJ133492. The allele DRB1*04new is a novel allele that has not been previously described.

The present invention also discloses the sequence of exon 2 of the HLA allele DRB4*01new. This sequence is identified by SEQ ID NO 67 and is shown below.

```
                                                        (SEQ ID NO 67)
 5                    10                   15                  20      (47)
CA CGT TTC TTG GAG CAG GCT AAG TGT GAG TGT CAT TTC CTC AAT GGG 25                   30                  35      (92)
    ACG GAG CGA GTG TGG AAC CTG ATC AGA TAC ATC TAT AAC CAA GAG 40                   45                  50     (137)
    GAG TAC GCG CGC TAC AAC AGT GAT CTG GGG GAG TAC CAG GCG GTG 55                   60                  65     (182)
    ACG GAG CTG GGG CGG CCT GAC GCT GAG TAC TGG AAC AGC CAG AAG 70                   75                  80     (227)
    GAC CTC CTG GAG CGG AGG CGG GCC GAG GTG GAC ACC TAC TGC AGA 85                   90                  95     (270)
    TAC AAC TAC GGG GTT GTG GAG AGC TTC ACA GTG CAG CGG CGA G
```

The sequence is shown from 5' to 3' and runs from codon 5 to codon 95 of exon 2. The numbering of the codons is indicated. The nucleotide positions are indicated between brackets. This sequence has been submitted to the EMBL database and was assigned the accession number AJ131789. The allele DRB4*01new is a novel allele that has not been previously described.

Having knowledge of this sequence information, the skilled man will be able to devise methods that enable typing of said allele. The present invention thus relates to a method for typing of the alleles HLA-DRB1*0820, HLA-DRB1*04new and/or HLA-DRB4*01new in a sample.

According to a preferred embodiment, the present invention relates to a method for typing of the alleles HLA-DRB1*0820, HLA-DRB1*04new and/or HLA-DRB4*01new in a sample, with said method comprising:
  i) amplifying a fragment comprising all or part of exon 2 of said allele using at least one suitable pair of primers;
  ii) hybridizing the amplified product of step i) to a set of probes, with the probes of said set specifically hybridizing to target regions comprising one or more polymorphic nucleotides in exon 2 of said allele;
  iii) determining from the result of step ii) the presence or absence of the alleles HLA-DRB1*0820, HLA-DRB1*04new and/or HLA-DRB4*01new in the sample.

The primers used in this method may be generic primers, i.e. primers that hybridize to target regions that are conserved, at least towards their 3'-end, amongst all members of a group of alleles (e.g. the DPB group or the DQB group or the DRB group) and thus will lead to amplification of all alleles within this group. Alternatively the primers may be subgroup-specific, i.e. primers that hybridize to target sequences that are only present in a subgroup of alleles. Such subgroup-specific primers can be used separately, or more than one 5'-primer or more than one 3'-end primer can be used together in a mix. Such a mix is sometimes called a multiplex primer. Different types of primers may be used in combination, e.g. a multiplex 5'-primer may be used with a generic 3'-primer, etc.

According to a more preferred embodiment, the present invention relates to a method as defined above, further characterized in that the primers used for the amplification of exon 2 of DRB1*0820, HLA-DRB1*04new and/or HLA-DRB4*01new are chosen from Table 1.

TABLE 1

Primers for amplification of exon2 of the HLA-allele DRB1*0820, the HLA-allele DRB1*04new and/or the HLA-allele DRB4*01new.

| Primer | Position[1] and sequence | SEQ ID NO |
|---|---|---|
| DRBp5'gen | intron-GATCCTTCGTGTCCCCACAGCACG-6 | SEQ ID NO 3 |
| DRBp5'intron | intron-ACCGGATCCTTCGTGTCCCCACAG-5 | SEQ ID NO 53 |
| DRBp5'DR3,8,11,12,13,14 | intron-CCCCACAGCACGTTTCTTGGAGTACTC-11 | SEQ ID NO 4 |
| DRBp5'DR1,7 | intron-TGTCCCCACAG CA CGT TTC TTG TG-9 | SEQ ID NO 5 |
| DRBp5'DR4 | 6-T TTC TTG GAG CAG GTT AAA C-13 | SEQ ID NO 6 |
| DRBp5'DR4 | 5-A CGT TTC TTG GAG CAG GTT AAA C-13 | SEQ ID NO 52 |
| DRBp5'DR9 | 5-CA CGT TTC TTG AAG CAG GAT AAG TT-13 | SEQ ID NO 7 |
| DRBp5'DR10 | intron-CACAG CA CGT TTC TTG GAG G-10 | SEQ ID NO 8 |
| DRBp5'DR15,16 | 8-CTG TGG CAG CCT AAG AGG-13 | SEQ ID NO 9 |
| DRB4p5' | 9-TAAGTGTGAGTGTCATTTC-17 | SEQ ID NO 54 |
| DRBp3'gen | 94-TCGCCGCTGCACTGTGAAGCTC-87 | SEQ ID NO 10 |
| DRBp3'DRB1 | intron-ATTCCCGCGCCGCGCT-intron | SEQ ID NO 11 |
| DRB3'cod86V | 92-CTGCACTGTGAAGCTCTCCA-86 | SEQ ID NO 12 |
| DRBp3'intron | intron-CCCGCCCTCCACCATGCTCAC-95 | SEQ ID NO 107 |

[1]The numbers before and after the sequences indicate the codons where the 5'-ends and the 3'-ends of the primers are located. "Intron" means that the 5'-end and/or the 3'-end is/are located in an intron.

SEQ ID NO 3 and SEQ ID NO 53 are generic primers that have a target region covering the junction of intron 1 and exon 2. This target region is conserved amongst all DRB alleles (DRB 1, DRB3, DRB4 and DRB5). SEQ ID NOs 4 to 9 and SEQ ID NOs 4, 5, 52, 7, 8, 9 constitute multiplex primer mixes, which hybridize to the subclasses DR1, DR3, DR4, DR7, DR8, DR9, DR10, DR11, DR12, DR13, DR14, DR15 and DR16. Together these subclasses constitute the group of DRB1 alleles. SEQ ID NO 4 is the only member of these primer mixes that specifically hybridizes to the allele HLA-DRB1*0820. SEQ ID NOs 6 and 52 are the only members of the primer mixes that specifically hybridize to the allele HLA-DRB1*04new. SEQ ID NO 54 specifically hybridizes to the allele HLA-DRB4. These specific primers can be used separately or in a mix such as described above. SEQ ID NO 10 is a generic primer that has its target region at codon 94 to codon 87 in exon 2. This target region is conserved amongst all DRB alleles. SEQ ID NO 11 is situated in intron 2, and hybridizes to all DRB1 alleles. The target region of SEQ ID NO12 is situated at codon 92 to codon 86. Codon 86 is a dimorphic codon that either encodes a Val or a Gly. SEQ ID NO 12 hybrizes to the codon encoding Val. SEQ ID NO 107 is situated in intron 2 and hybridizes to all DRB alleles.

According to another more preferred embodiment, the present invention relates to a method as defined above, further characterized in that said polymorphic nucleotides have: the following positions in SEQ ID NO 1 and SEQ ID NO 67:

9, 12, 13, 15, 16, 17, 18, 19, 22, 23, 24, 25, 26, 27, 29, 33, 35, 44, 61, 64, 65, 67, 69, 71, 75, 76, 78, 81, 84, 89, 92, 95, 96, 97, 99, 100, 104, 106, 127, 136, 146, 156, 157, 158, 160, 161, 162, 165, 166, 186, 194, 195, 196, 197, 198, 199, 203, 205, 207, 208, 209, 217, 218, 219, 220, 221, 237, 239, 241, 244, 245, 251, 257; and the following positions in SEQ ID NO 50:

5, 8, 9, 11, 12, 13, 14, 15, 18, 19, 20, 21, 22, 23, 25, 29, 31, 40, 57, 60, 61, 63, 65, 67, 71, 72, 74, 77, 80, 85, 88, 91, 92, 93, 95, 96, 100, 102, 123, 132, 142, 152, 153, 154, 156, 157, 158, 161, 162, 182, 190, 191, 192, 193, 194, 195, 199, 201, 203, 204, 205, 213, 214, 215, 216, 217, 233, 235, 237, 240, 241.

These nucleotides are shown in boldface in the sequences above (SEQ ID NOs 1, 50 and 67).

According to an even more preferred embodiment, the present invention relates to a method as defined above, further characterized in that said probes that specifically hybridize to a target region comprising one or more polymorphic nucleotides in exon 2 of the allele DRB1*0820, are chosen from Table 2.

TABLE 2

Oligonucleotide probes that can be used for typing of the HLA-allele DRB1*0820.

| Ref. No | Position¹ and sequence | SEQ ID NO |
|---|---|---|
| 9 | 9-G TAC TCT ACG TCT GAG TG-15 | SEQ ID NO 13 |
| 26 | 54-G CCT GAT GCC GAG TAC TGG-61 | SEQ ID NO 14 |
| 25 | 64-AG AAG GAC TTC CTG GAA GA-70 | SEQ ID NO 15 |
| 21 | 69-A GCC AGG CGG GCC CTG GTG GA-76 | SEQ ID NO 16 |
| 44 | 84-GGG GTT GTG GAG AGC-88 | SEQ ID NO 17 |
|  | 17-TTC TTC AAT GGG ACG GAG-22 | SEQ ID NO 18 |
|  | 26-TTC CTG GAC AGA TAC TTC-31 | SEQ ID NO 19 |
|  | 34-CAA GAG GAG TAC GTG CGC-39 | SEQ ID NO 20 |
|  | 45-GGG GAG TAC CGG GCG GTG-50 | SEQ ID NO 21 |

¹The sequences are given from 5' to 3'. The numbers before and after the sequences indicate the codons where the 5'-ends and the 3'-ends of the probes are located.

According to another even more preferred embodiment, the present invention relates to a method as defined above, further characterized in that said probes that specifically hybridize to a target region comprising one or more polymorphic nucleotides in exon 2 of the allele DRB1*04new, are chosen from Table 3.

TABLE 3

Oligonucleotide probes that can be used for typing of the HLA-allele DRB1*04new.

| Ref. No | Position¹ and sequence | SEQ ID NO |
|---|---|---|
| 15 | 70-CAG AAG CGG GCC GCG-74 | SEQ ID NO 55 |
| 24 | 32-AT CAC CAA GAG GAG TAC GTG-38 | SEQ ID NO 56 |

TABLE 3-continued

Oligonucleotide probes that can be used for typing of the HLA-allele DRB1*04new.

| Ref. No | Position¹ and sequence | SEQ ID NO |
|---|---|---|
| 27 | 81-CAC AAC TAC GGG GTT GGT GA-87 | SEQ ID NO 57 |
| 36 | 55-G CCT GAT GCC GAG TAC TGG-61 | SEQ ID NO 58 |
| 49 | 73-GCC GCG GTG GAC ACC-77 | SEQ ID NO 59 |
| 63 | 63-C CAG AAG GAC CTC CTG GA-69 | SEQ ID NO 60 |
| 73 | 28-C AGA TAC TTC TAT CAC CAA GA-35 | SEQ ID NO 61 |

¹The sequences are given from 5' to 3'. The numbers before and after the sequences indicate the codons where the 5'-ends and the 3'-ends of the probes are located.

According to another even more preferred embodiment, the present invention relates to a method as defined above, further characterized in that said probes that specifically hybridize to a target region comprising one or more polymorphic nucleotides in exon 2 of the allele DRB4*01new, are chosen from Table 4.

TABLE 4

Oligonucleotide probes that can be used for typing of the HLA-allele DRB4*04new.

| Ref. No | Position¹ and sequence | SEQ ID NO |
|---|---|---|
| 15 | 72-GG GCC GAG GTG GAC A-77 | SEQ ID NO 62 |
| 36 | 63-C CAG AAG GAC CTC CTG GA-69 | SEQ ID NO 63 |
| 44 | 84-GGG GTT GTG GAG AGC-88 | SEQ ID NO 64 |
| 60 | 35-GAG GAG TAC GCG CGC T-40 | SEQ ID NO 65 |
| 62 | 22-GAG CGA GTG TGG AAC C-27 | SEQ ID NO 66 |

¹The sequences are given from 5' to 3'. The numbers before and after the sequences indicate the codons where the 5'-ends and the 3'-ends of the probes are located.

These probes hybridize to target regions comprising polymorphic nucleotides in exon 2. The set of probes with SEQ ID NOs 13 to SEQ ID NO 17 yield a unique hybridization pattern for the allele DRB 1*0820, that allows discrimination of this allele from all other DRBI alleles at the allelic level. The set of probes with SEQ ID NO 55 to SEQ ID NO 61 yield a unique hybridization pattern for the allele DRBI*04new, that allows discrimination of this allele from all other DRB 1 alleles at the allelic level. The set of probes with SEQ ID NO 62 to SEQ ID NO 66 yield a unique hybridization pattern for the allele DRB4*01 new, that allows discrimination of this allele from all other DRB4 alleles at the allelic level. At present, 215 different DRBI alleles and 8 different DRB4 alleles have been described (URL: ebi[dot]ac[dot]uk[slash]imgt[slash]hla[slash]). The probes with SEQ ID NOs 13 to 17 and 55 to 66 are part of the DRB decoder kit (2nd generation) of Innogenetics NV (Ghent, Belgium), which comprises 62 probes. SEQ ID NOs 13 to 17 constitute a subgroup of probes of this kit that specifically hybridize to the allele DRB 1*0820. SEQ ID NOs 55 to 61 constitute a subgroup of probes of this kit that specifically hybridize to the allele DRB 1*04new. SEQ ID NOs 62 to 66 constitute a subgroup of probes of this kit that specifically hybridize to the allele DRB4*01 new. The probes with SEQ ID NOs 13 to 17 and 55 to 66 have been optimized to function in combination at the same conditions in a LiPA assay (see below).

The skilled man will recognize that the probes and primers with SEQ ID NOs 3 to 21 and 52 to 66 may be adapted by addition or deletion of one or more nucleotides at their extremities. Such adaptations may be required, for instance, if the conditions of amplification or hybridization are changed, or if the amplified material is RNA instead of DNA, as is the case in the NASBA system. Different techniques can be applied to perform the methods of the present invention. These techniques may comprise immobilizing the HLA polynucleic acids, possibly after amplification, on a solid support and performing hybridization with labelled oligonucleotide probes. Alternatively, the probes may be immobilized on a solid support and hybridization may be performed with labelled HLA polynucleic acids, possibly after amplification. This technique is called reverse hybridization. A convenient reverse hybridization technique is the line probe assay (LiPA). This assay uses oligonucleotide probes immobilized as parallel lines on a solid support strip (Stuyver et al., 1993). It is to be understood that any other technique for detection of the above-mentioned HLA allele is also covered by the present invention.

The present invention also relates to any primer or any probe as indicated above, for use in a method for typing of the alleles HLA-DRB1*0820, HLA DRB1*04new and/or HLA-DRB4*01new. The invention further relates to an isolated polynucleic acid, defined by SEQ ID NOs 1, 50 and 67, corresponding to exon 2 of the allele HLA-DRB1*0820, HLA DRB1*04new and HLA-DRB4*01new, respectively. The invention also relates to any fragment thereof that can be used as a primer or as a probe in a method for typing of said allele.

Furthermore, having access to the isolated polynucleic acids defined by SEQ ID NO 1, a man skilled in the art will be able to isolate the complete HLA-DRB1*0820 gene from a human genomic library. Having access to the isolated polynucleic acid defined by SEQ ID NO 50, a man skilled in the art will be able to isolate the complete HLA-DRB1*04new gene from a human genomic library. Having access to the isolated polynucleic acid defined by SEQ ID NO 67, a man skilled in the art will be able to isolate the complete HLA-DRB4*01new gene from a human genomic library. This can be done by screening of the library with the polynucleic acid defined by respectively SEQ ID NO 1, SEQ ID NO 50 or SEQ ID NO 67 or suitable fragments thereof as a hybridisation probe. The present invention thus also relates to the complete HLA-DRB1*0820 gene, the complete HLA-DRB1*04new gene and the complete HLA-DRB4*01new gene.

According to another preferred embodiment, the present invention relates to a diagnostic kit enabling typing of the alleles HLA-DRB1*0820, HLA-DRB1*04new and/or HLA-DRB4*01new, with said kit comprising at least one primer and/or at least one probe as indicated above. Optionally, this kit may also comprise an enzyme and/or reagents enabling the amplification step and/or reagents enabling the hybridization step.

According to another preferred embodiment, the present invention relates to the protein fragment that is encoded by SEQ ID NO 1. The sequence of this fragment can be obtained by converting the nucleic acid sequence of SEQ ID NO 1 into the corresponding amino acid sequence, whereby the reading frame to be used is as indicated above. The amino acid sequence is shown below as SEQ ID NO 2.

```
                                        (SEQ ID NO 2)
R F L E Y S T S E C H F F N G T E R V

R F L D R Y F Y N Q E E Y V R F D S D V

G E Y R A V T E L G R P D A E Y W N S Q

K D F L E D R R A L V D T Y C R H N Y G

V V E S F T V Q R R
```

According to another preferred embodiment, the present invention relates to the protein fragment that is encoded by SEQ ID NO 50. The sequence of this fragment can be obtained by converting the nucleic acid sequence of SEQ ID NO 50 into the corresponding amino acid sequence, whereby the reading frame to be used is as indicated above. The amino acid sequence is shown below as SEQ ID NO 51.

```
                                        (SEQ ID NO 51)
F L E Q V K P E C H F F N G T E R V

R F L D R Y F Y H Q E E Y V R F D S D V

G E Y R A V T E L G R P D A E Y W N S Q

K D L L E Q K R A A V D T Y C R H N Y G

V G
```

According to another preferred embodiment, the present invention thus also relates to a method for detection of the protein fragments identified as SEQ ID NO 2 and/or SEQ ID NO 51 in a sample. Said method may be one of the well-known serological methods mentioned above (Terasaki and McClelland, 1964; Kissmeyer et al., 1969).

In accordance the present invention also relates to an antiserum or a ligand binding to the protein fragment according to the invention. The term "a ligand" refers to any molecule able to bind the protein fragment of the present invention. The latter term specifically refers to polyclonal and/or monoclonal antibodies specifically raised (by any method known in the art) against the protein fragment of the present invention and also encompasses any antibody-like, and other, constructs as described in detail in WO 98/58965 to Lorré et al.

The present invention further relates to a kit for the detection of one or more of the protein fragments of the invention, comprising at least an antiserum or a ligand as described above.

The present invention also discloses the sequence of exon 2 and of exon 3 of the HLA allele B*3913. These sequences are identified by SEQ ID NOs 22 and 23 and are shown below.

```
                                                       (SEQ ID NO 22)
         10         20         30         40         50         60
GCTCCCACTC CATGAGGTAT TTCTACACCT CCGTGTCCCG GCCCGGCCGC GGGGAGCCCC 70         80         90        100        110        120
GCTTCATCTC AGTGGGCTAC GTGGACGACA CGCAGTTCGT GAGGTTCGAC AGCGACGCCG 130        140        150        160        170        180
CGAGTCCGAG AGAGGAGCCG CGGGCGCCGT GGATAGAGCA GGAGGGGCCG GAGTATTGGG
```

```
                    190        200        210        220        230        240
          ACCGGGAGAC ACAGATCTCC AAGACCAACA CACAGACTTA CCGAGAGAGC CTGCGGAACC 250        260        270
          TGCGCGGCTA CTACAACCAG AGCGAGGCCG exon 2

(SEQ ID NO 23)
                     10         20         30         40         50         60
          GGTCTCACAC CCTCCAGAGG ATGTACGGCT GCGACGTGGG GCCGGACGGG CGCCTCCTCC 70         80         90        100        110        120
          GCGGGCATAA CCAGTTCGCC TACGACGGCA AGGATTACAT CGCCCTGAAC GAGGACCTGA 130        140        150        160        170        180
          GCTCCTGGAC CGCGGCGGAC ACCGCGGCTC AGATCACCCA GCGCAAGTGG GAGGCGGCCC 190        200        210        220        230        240
          GTGTGGCGGA GCAGCTGAGA ACCTACCTGG AGGGCACGTG CGTGGAGTGG CTCCGCAGAT 250        260        270
          ACCTGGAGAA CGGGAAGGAG ACGCTGCAGC GCGCGG exon 3
```

These sequences are shown from 5' to 3'. These sequences have been submitted to the EMBL database and were assigned the accession number AJ223282. The allele HLA-B*3913 is a novel allele that has not been previously described.

The present invention also discloses the sequence of exon 2 and of exon 3 of the HLA allele B*1406. These sequences are identified by SEQ ID NOs 72 and 73 and are shown below.

```
                                                              (SEQ ID NO 72)
                     10         20         30         40         50         60
          GCTCCCACTC CATGAGGTAT TTCTACACCG CCGTGTCCCG GCCCGGCCGC GGGGAGCCCC 70         80         90        100        110        120
          GCTTCATCTC AGTGGGCTAC GTGGACGACA CGCAGTTCGT GAGGTTCGAC AGCGACGCCG 130        140        150        160        170        180
          CGAGTCCGAG AGAGGAGCCG CGGGCGCCGT GGATAGAGCA GGAGGGGCCG GAATATTGGG 190        200        210        220        230        240
          ACCGGAACAC ACAGATCTGC AAGACCAACA CACAGACTGA CCGAGAGAGC CTGCGGAACC 250        260        270
          TGCGCGGCTA CTACAACCAG AGCGAGGCCG exon 2

(SEQ ID NO 73)
                     10         20         30         40         50         60
          GGTCTCACAC CCTCCAGAGG ATGTACGGCT GCGACGTGGG GCCGGACGGG CGCCTCCTCC 70         80         90        100        110        120
          GCGGGTATAA CCAGTTCGCC TACGACGGCA AGGATTACAT CGCCCTGAAC GAGGACCTGA 130        140        150        160        170        180
          GCTCCTGGAC CGCGGCGGAC ACCGCGGCTC AGATCACCCA GCGCAAGTGG GAGGCGGCCC 190        200        210        220        230        240
          GTGAGGCGGA GCAGCTGAGA GCCTACCTGG AGGGCACGTG CGTGGAGTGG CTCCGCAGAC 250        260        270
          ACCTGGAGAA CGGGAAGGAG ACGCTGCAGC GCGCGG exon 3
```

These sequences are shown from 5' to 3'. These sequences have been submitted to the EMBL database and were assigned the accession numbers AJ131193 for exon 2 and AJ131194 for exon 3. The allele HLA-B*1406 is a novel allele that has not been previously described.

The present invention also discloses the sequence of exon 2 and of exon 3 of the HLA allele B*51new. These sequences are identified by SEQ ID NOs 74 and 75 and are shown below.

```
                                                    (SEQ ID NO 74)
         10         20         30         40         50         60
GCTCCCACTC CATGAGGTAT TTCTACACCG CCATGTCCCG GCCCGGCCGC GGGGAGCCCC 70         80         90        100        110        120
GCTTCATTGC AGTGGGCTAC GTGGACGACA CCCAGTTCGT GAGGTTCGAC AGCGACGCCG 130        140        150        160        170        180
CGAGTCCGAG GACGGAGCCC CGGGCGCCAT GGATAGAGCA GGAGGGGCCG GAGTATTGGG 190        200        210        220        230        240
ACCGGAACAC ACAGATCTTC AAGACCAACA CACAGACTTA CCGAGAGAAC CTGCGGATCG 250        260        270
CGCTCCGCTA CTACAACCAG AGCGAGGCCG exon 2

(SEQ ID NO 75)
         10         20         30         40         50         60
GGTCTCACAC TTGGCAGACG ATGTATGGCT GCGACGTGGG GCCGGACGGG CGCCTCCTCC 70         80         90        100        110        120
CCGGGCATAA CCAGTACGCC TACGACGGCA AAGATTACAT CGCCCTGAAC GAGGACCTGA 130        140        150        160        170        180
GCTCCTGGAC CGCGGCGGAC ACCGCGGCTC AGATCACCCA GCGCAAGTGG GAGGCGGCCC 190        200        210        220        230        240
GTGAGGCGGA GCAGCTGAGA GCCTACCTGG AGGGCCTGTG CGTGGAGTGG CTCCGCAGAC 250        260        270
ACCTGGAGAA CGGGAAGGAG TCGCTGCAGC GCGCGG exon 3
```

These sequences are shown from 5' to 3'. The allele HLA-B*51new is a novel allele that has not been previously described.

Having knowledge of this sequence information, the skilled man will be able to devise methods that enable typing of said alleles. The present invention thus relates to a method for typing of the alleles HLA-B*3913, HLA-B*1406 and/or HLA-B*51new in a sample.

According to a preferred embodiment, the present invention relates to a method for typing of the alleles HLA-B*3913, HLA-B*1406 and/or HLA-B*51new in a sample, with said method comprising:
i) amplifying a fragment of said allele comprising all or part of exon 2 and/or all or part of exon 3 of said allele using at least one suitable pair of primers;
ii) hybridizing the amplification product of step i) to at least one probe that specifically hybridizes to a target region comprising one or more polymorphic nucleotides in exon 2 or in exon 3 of said allele;
iii) determining from the result of step ii) the presence or absence of the allele HLA-B*3913, HLA-B*1406 and/or HLA-B*51new in the sample.

The primers used in this method may be generic primers, i.e. primers that hybridize to target regions that are conserved, at least towards their 3'-end, amongst all alleles of a given locus (e.g. the HLA-A alleles or the HLA-B alleles or the HLA-C alleles) and thus will lead to amplification of all alleles of this locus. Alternatively the primers may be sub-group-specific, i.e. primers that hybridize to target sequences that are only present in a subgroup of alleles. These subgroup-specific primers can be used separately, or more than one 5'-primer or more than one 3'-end primer can be used together in a mix. Such a mix is sometimes called a multiplex primer. Different types of primers may be used in combination, e.g. a multiplex 5'-primer may be used with a generic 3'-primer.

According to a more preferred embodiment, the present invention relates to a method as defined above, further characterized in that the primers used are chosen from Table 5.

TABLE 5

Primers for amplification of exon2/exon 3 of the HLA-allele B*3913, the HLA-allele B*1406 and/or the HLA-allele B*51new.

| Name | Sequence | SEQ ID NO |
|---|---|---|
| IBPIN1 | GGGAGGAGCGAGGGGACCSCAC (S = G OR C) | SEQ ID NO 26 |
| IBPIN3 | GGAGGCCATCCCCGGCGACCTAT | SEQ ID NO 27 |

IBPEM1 is a 5'-primer, located upstream of exon 2 and IBPIN3 is a 3'-primer, located downstream of exon 3 These are generic primers, enabling amplification of a fragment of all 274 HLA-B alleles that are presently known (URL: ebi[dot]ac[dot]uk[slash]imgt[slash]hla[slash])

According to another more preferred embodiment, the present invention relates to a method as defined above, further characterized in that:
said polymorphic nucleotides have the following positions in exon 2:
11, 24, 30, 33, 44, 46, 68, 69, 71, 88, 92, 94, 102, 120, 131, 132, 133, 136, 140, 149, 153, 155, 161, 173, 174, 183, 186, 188, 190, 193, 196, 197, 198, 199, 200, 204, 205, 207, 208, 209, 210, 212, 219, 226, 228, 229, 236, 238, 240, 241, 244, 246, 268, and/or
said polymorphic nucleotides have the following positions in exon 3:

2, 10, 11, 12, 13, 14, 18, 19, 20, 26, 36, 44, 54, 66, 68, 69, 75, 76, 77, 92, 120, 134, 141, 142, 145, 156, 159, 163, 169, 184, 195, 196, 197, 201, 214, 216, 217, 227, 228, 229, 240.

These polymorphic nucleotides are shown in boldface in the sequences above (SEQ ID NOs 22 and 23, SEQ ID NOs 72 and 73, and SEQ ID NOs 74 and 75).

According to another even more preferred embodiment, the present invention relates to a method as defined above, further characterized in that said probes that specifically hybridize to a target region comprising one or more polymorphic nucleotides in exon 2 or exon 3 of the allele HLA-B*3913, are chosen from Table 6.

TABLE 6

Oligonucleotide probes that can be used for typing of the HLA-allele B*3913.

| Reference | Sequence[1] | SEQ ID NO |
|---|---|---|
| 56 | GGGACACGGAGGTGTAGA | SEQ ID NO 28 |
| 92 | CCGGCCCGGCCGCGGG | SEQ ID NO 29 |
| 2 | GCTTCATCTCAGTGGGCT | SEQ ID NO 30 |
| HC | GTTCGTGAGGTTCGACA | SEQ ID NO 31 |
| 7 | GAGTCCGAGAGAGGAGCCG | SEQ ID NO 32 |
| 87 | GGCCGGAGTATTGGGAC | SEQ ID NO 33 |
| 10 | GGACCGGGAGACACAGAT | SEQ ID NO 34 |
| 13 | AGATCTCCAAGACCAAC | SEQ ID NO 35 |
| 18 | CACAGACTTACCGAGAG | SEQ ID NO 36 |
| 19 | ACCGAGAGAGCCTGCGG | SEQ ID NO 37 |
| 50 | CGGAACCTGCGCGGCTA | SEQ ID NO 38 |
| 26 | AGAGGATGTACGGCTGC | SEQ ID NO 39 |
|  | GACGTGGGGCCGGACG | SEQ ID NO 40 |
| 91 | GACGGGCGCCTCCTCCG | SEQ ID NO 41 |
| 28 | TCCTCCGCGGGCATAACCAG | SEQ ID NO 42 |
| 53 | GGGCATAACCAGTTCGCCT | SEQ ID NO 43 |
| 90 | GAGGACCTGAGCTCCTGG | SEQ ID NO 44 |
| 38 | CGGCCCGTGTGGCGGAG | SEQ ID NO 45 |
| 88 | GCAGCTGAGAACCTACCT | SEQ ID NO 46 |
| 36 | TGGAGGGCACGTGCGTG | SEQ ID NO 47 |
|  | CGTGGAGTGGCTCCGC | SEQ ID NO 48 |
|  | TCCGCAGATACCTGGAGA | SEQ ID NO 49 |

[1]The sequences are given from 5' to 3'.

These probes hybridize to target regions comprising polymorphic nucleotides in exon 2 or exon 3 of the allele B*3913. All probes are sense probes, i.e. hybridizing to the anti-sense strand, except the probe with SEQ ID NO 28, which is an anti-sense probe. The probes with SEQ ID NOs 28 to 49 have been optimized to function under the same conditions in a LiPA assay (see below).

According to another even more preferred embodiment, the present invention relates to a method as defined above, further characterized in that said probes that specifically hybridize to a target region comprising one or more polymorphic nucleotides in exon 2 or exon 3 of the allele HLA-B*1406, are chosen from Table 7.

TABLE 7

Oligonucleotide probes that can be used for typing of the HLA-allele B*1406.

| Reference | Sequence[1] | SEQ ID NO |
|---|---|---|
| B75 | TCTACACCGCCGTGTCC | SEQ ID NO 76 |
| B92 | CCGGCCCGGCCGCGGG | SEQ ID NO 29 |
| B2 | GCTTCATCTCAGTGGGCT | SEQ ID NO 30 |
| B85 | GCGACGCCGCGAGTCCGA | SEQ ID NO 77 |
| B7 | GAGTCCGAGAGAGGAGCCG | SEQ ID NO 32 |
| B98 | GGCCGGAATATTGGGAC | SEQ ID NO 78 |
| B9 | GGACCGGAACACACAG | SEQ ID NO 79 |
| B16 | ACAGATCTGCAAGACCA | SEQ ID NO 80 |
| B17 | ACAGACTGACCGAGAG | SEQ ID NO 81 |
| B19 | ACCGAGAGAGCCTGCGG | SEQ ID NO 37 |
| B56 | GGAACCTGCGCGGCTACTA | SEQ ID NO 82 |
| B26 | AGAGGATGTACGGCTG | SEQ ID NO 83 |
| B89 | CGACGTGGGGCCGGACG | SEQ ID NO 84 |
| B91 | GACGGGCGCCTCCTCCG | SEQ ID NO 41 |
| B63 | GGGTATAACCAGTTCGCCT | SEQ ID NO 85 |
| B90 | AGGACCTGAGCTCCTGG | SEQ ID NO 86 |
| B31 | GCCCGTGAGGCGGAGC | SEQ ID NO 87 |
| B66 | GCAGCTGAGAGCCTACCT | SEQ ID NO 88 |
| B36 | TGGAGGGCACGTGCGTG | SEQ ID NO 47 |
| B88 | CGTGGAGTGGCTCCGC | SEQ ID NO 48 |
| B70 | CCGCAGACACCTGGAGA | SEQ ID NO 89 |

[1]The sequences are given from 5' to 3'.

These probes hybridize to target regions comprising polymorphic nucleotides in exon 2 or exon 3 of the allele B*1406. All probes are sense probes, i.e. hybridizing to the anti-sense strand. The probes with SEQ ID NOs 30, 32, 79, 80, 81, 37, 82, 83, 87, 47 and 89 have been optimized to function under the same conditions in a LiPA assay (see below).

According to another even more preferred embodiment, the present invention relates to a method as defined above, further characterized in that said probes that specifically hybridize to a target region comprising one or more polymorphic nucleotides in exon 2 or exon 3 of the allele HLA-B*51new, are chosen from Table 8.

TABLE 8

Oligonucleotide probes that can be used for typing of the HLA-allele B*51new.

| Reference | Sequence[1] | SEQ ID NO |
|---|---|---|
| B3 | GCTTCATTGCAGTGGGCT | SEQ ID NO 90 |
| B6 | CGAGTCCGAGGACGGAGCCCGG | SEQ ID NO 91 |

TABLE 8-continued

Oligonucleotide probes that can be used for typing of the HLA-allele B*51new.

| Reference | Sequence[1] | SEQ ID NO |
|---|---|---|
| B9  | GGACCGGAACACACAG | SEQ ID NO 79 |
| B14 | CAGATCTTCAAGACCAAC | SEQ ID NO 92 |
| B18 | CACACAGACTTACCGAGAG | SEQ ID NO 93 |
| B51 | CGAGAGAACCTGCGGATC | SEQ ID NO 94 |
| B55 | CGGATCGCGCTCCGCTA | SEQ ID NO 95 |
| B73 | TCTACACCGCCATGTCC | SEQ ID NO 96 |
| B85 | GCGACGCCGCGAGTCCG | SEQ ID NO 97 |
| B87 | GGCCGGAGTATTGGGAC | SEQ ID NO 33 |
| B23 | ACACTTGGCAGACGATG | SEQ ID NO 98 |
| B31 | GCCCGTGAGGCGGAGC | SEQ ID NO 87 |
| B35 | GGAGGGCCTGTGCGTG | SEQ ID NO 99 |
| B60 | CATAACCAGTACGCCTACG | SEQ ID NO 100 |
| B70 | CCGCAGACACCTGGAGA | SEQ ID NO 89 |
| B88 | GTGGAGTGGCTCCGC | SEQ ID NO 101 |
| B89 | CGACGTGGGGCCGGACG | SEQ ID NO 84 |
| B90 | GAGGACCTGAGCTCCTGG | SEQ ID NO 44 |
| B91 | GACGGGCGCCTCCTCC | SEQ ID NO 102 |

[1]The sequences are given from 5' to 3'.

These probes hybridize to target regions comprising polymorphic nucleotides in exon 2 or exon 3 of the allele B*51new. All probes are sense probes, i.e. hybridizing to the anti-sense strand, except the probe with SEQ ID NO 97, which is an anti-sense probe. The probes with SEQ ID NOs 90, 91, 79, 92, 93, 98, 87, 99, 94, 95, 100 and 89 have been optimized to function under the same conditions in a LiPA assay (see below).

The skilled man will recognize that the probes and primers with SEQ ID NOs 26 to 49 and SEQ ID NOs 76 to 102 may be adapted by addition or deletion of one or more nucleotides at their extremities. Such adaptations may be required, for instance, if the conditions of amplification or hybridization are changed, or if the amplified material is RNA instead of DNA, as is the case in the NASBA system.

Different techniques can be applied to perform the methods of the present invention. These techniques may comprise immobilizing the HLA polynucleic acids, possibly after amplification, on a solid support and performing hybridization with labelled oligonucleotide probes. Alternatively, the probes may be immobilized on a solid support and hybridization may be performed with labelled HLA polynucleic acids, possibly after amplification. This technique is called reverse hybridization. A convenient reverse hybridization technique is the line probe assay (LiPA). This assay uses oligonucleotide probes immobilized as parallel lines on a solid support strip (Stuyver et al., 1993). It is to be understood that any other technique for detection of the above-mentioned HLA allele is also covered by the present invention.

The present invention also relates to any primer or any probe as indicated above, for use in a method for typing of the alleles HLA-B*3913, HLA-B*1406 and/or HLA-B*51new.

The invention further relates to an isolated polynucleic acid, defined by SEQ ID NO 22, corresponding to exon 2 of the allele HLA-B*3913, and to an isolated polynucleic acid, defined by SEQ ID NO 23, corresponding to exon 3 of said allele, or to any fragment of said polynucleic acids that can be used as a primer or as a probe in a method for typing of said allele. The invention also relates to an isolated polynucleic acid, defined by SEQ ID NO 72, corresponding to exon 2 of the allele HLA-B*1406, and to an isolated polynucleic acid, defined by SEQ ID NO 73, corresponding to exon 3 of said allele, or to any fragment of said polynucleic acids that can be used as a primer or as a probe in a method for typing of said allele. The invention also relates to an isolated polynucleic acid, defined by SEQ ID NO 74, corresponding to exon 2 of the allele HLA-B*51new, and to an isolated polynucleic acid, defined by SEQ ID NO 75, corresponding to exon 3 of said allele, or to any fragment of said polynucleic acids that can be used as a primer or as a probe in a method for typing of said allele.

Furthermore, having access to the isolated polynucleic acids defined by SEQ ID NO 22 and SEQ ID NO 23, a man skilled in the art will be able to isolate the complete HLA-B*3913 gene from a human genomic library. Having access to the isolated polynucleic acids defined by SEQ ID NO 72 and SEQ ID NO 73, a man skilled in the art will be able to isolate the complete HLA-B*1406 gene from a human genomic library. Having access to the isolated polynucleic acids defined by SEQ ID NO 74 and SEQ ID NO 75, a man skilled in the art will be able to isolate the complete HLA-B*51new gene from a human genomic library. This can be done by screening of the library with respectively the polynucleic acids defined by SEQ ID NO 22 or 23, the polynucleic acids defined by SEQ ID NO 72 or 73, or the polynucleic acids defined by SEQ ID NO 74 or 75, or by any suitable fragments thereof as a hybridisation probe. The present invention thus also relates to the complete HLA-B*3913, HLA-B*1406 and HLA-B*51new gene.

According to another preferred embodiment, the present invention relates to a diagnostic kit enabling typing of the alleles HLA-B*3913, HLA-B1406 and/or HLA-B*51new, with said kit comprising at least one primer and/or at least one probe as indicated above. Optionally, this kit may also comprise an enzyme and/or reagents enabling the amplification step and/or reagents enabling the hybridization step.

According to another preferred embodiment, the present invention relates to the protein fragments that are encoded by SEQ ID NO 22 or SEQ ID NO 23. The sequence of these fragments can be obtained by converting the nucleic acid sequences of SEQ ID NOs 22 or 23 into the corresponding amino acid sequences. The amino acid sequences are shown below as SEQ ID NOs 24 and 25 respectively.

(SEQ ID NO 24)
GSHSMRYFYT SVSRPGRGEP RFISVGYVDD TQFVRFDSDA

ASPREEPRAP WIEQEGPEYW DRETQISKTN TQTYRESLRN

LRGYYNQSEA (SEQ ID NO 25)
GSHTLQRMYG CDVGPDGRLL RGHNQFAYDG KDYIALNEDL

SSWTAADTAA QITQRKWEAA RVAEQLRTYL EGTCVEWLRR

YLENGKETLQ RA

According to another preferred embodiment, the present invention relates to the protein fragments that are encoded by SEQ ID NO 72 or SEQ ID NO 73. The sequence of these fragments can be obtained by converting the nucleic acid sequences of SEQ ID NOs 72 or 73 into the corresponding amino acid sequences. The amino acid sequences are shown below as SEQ ID NOs 103 and 104, respectively.

```
                                           (SEQ ID NO 103)
GSHSMRYSYT AVSRPGRGEP RFISVGYVDD TQFVRFDSDA

ASPREEPRAP WIEQEGPEYW DRNTQICKTN TQTDRESLRN

LRGYYNQSEA (SEQ ID NO 104)
GSHTLQRMYG CDVGPDGRLL RGYNQFAYDG KDYIALNEDL

SSWTAADTAA QITQRKWEAA REAEQLRAYL EGTCVEWLRR

HLENGKETLQ RA
```

According to another preferred embodiment, the present invention relates to the protein fragments that are encoded by SEQ ID NO 74 or SEQ ID NO 75. The sequence of these fragments can be obtained by converting the nucleic acid sequences of SEQ ID NOs 74 or 75 into the corresponding amino acid sequences. The amino acid sequences are shown below as SEQ ID NOs 105 and 106 respectively.

```
                                           (SEQ ID NO 105)
GSHSMRYFYT AMSRPGRGEP RFIAVGYVDD TQFVRFDSDA

ASPRTEPRAP WIEQEGPEYW DRNTQIFKTN TQTYRENLRI

ALRYYNQSEA (SEQ ID NO 106)
GSHTWQTMYG CDVGPDGRLL PGHNQYAYDG KDYIALNEDL

SSWTAADTAA QITQRKWEAA REAEQLRAYL EGLCVEWLRR

HLENGKESLQ RA
```

Accordingly, the present invention also relates to a method for detection of one or more of the protein fragments identified as SEQ ID NOs 24, 25, 103, 104, 105 and/or 106 in a sample. Said method may be one of the well-known serological methods mentioned above (Terasaki and McClelland, 1964; Kissmeyer et al., 1969).

In accordance the present invention also relates to an antiserum or a ligand binding to a polypeptide according to the invention. The term "a ligand" refers to any molecule able to bind the polypeptides of the present invention. The latter term specifically refers to polyclonal and/or monoclonal antibodies specifically raised (by any method known in the art) against the polypeptides of the present invention and also encompasses any antibody-like, and other, constructs as described in detail in WO 98/58965 to Lorréet al.

The present invention further relates to a kit for the detection of a polypeptide of the invention, comprising at least an antiserum or a ligand as described above.

DEFINITIONS

The following definitions and explanations will permit a better understanding of the present invention.

The target material in the samples to be analysed may either be DNA or RNA, e.g. genomic DNA, messenger RNA or amplified versions thereof. These molecules are in this application also termed "polynucleic acids".

Well-known extraction and purification procedures are available for the isolation of RNA or DNA from a sample (e.g. in Sambrook et al., 1989).

A "polymorphic nucleotide" refers to a nucleotide of the sequence of a given HLA allele that differs from at least one of the nucleotides that are found at the corresponding position in other HLA alleles of the same locus.

The term "typing" of an HLA-allele refers to identification of the allele, i.e. detection of the allele and discrimination of the allele from other alleles of the same locus.

The term "probe" according to the present invention refers to a single-stranded oligonucleotide which is designed to specifically hybridize to HLA polynucleic acids. Preferably, the probes of the invention are about 5 to 50 nucleotides long, more preferably from about 10 to 25 nucleotides. Particularly preferred lengths of probes include 10, 11, 12, 13, 14, 15, 16, 17, 18, 19, 20, 21, 22, 23, 24 or 25 nucleotides. The nucleotides as used in the present invention may be ribonucleotides, deoxyribonucleotides and modified nucleotides such as inosine or nucleotides containing modified groups which do not essentially alter their hybridization characteristics.

The term "primer" refers to a single stranded oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5-50 nucleotides long. Specific length and sequence will depend on the complexity of the required DNA or RNA targets, as well as on the conditions at which the primer is used, such as temperature and ionic strength. It is to be understood that the primers of the present invention may be used as probes and vice versa, provided that the experimental conditions are adapted.

The expression "suitable primer pair" in this invention refers to a pair of primers allowing specific amplification of a HLA polynucleic acid fragment.

The term "target region" of a probe or a primer according to the present invention is a sequence within the HLA polynucleic acids to which the probe or the primer is completely complementary or partially complementary (i.e. with some degree of mismatch). It is to be understood that the complement of said target sequence is also a suitable target sequence in some cases.

"Specific hybridization" of a probe to a target region of the HLA polynucleic acids means that said probe forms a duplex with part of this region or with the entire region under the experimental conditions used, and that under those conditions said probe does not form a duplex with other regions of the polynucleic acids present in the sample to be analysed.

"Specific hybridization" of a primer to a target region of the HLA polynucleic acids means that, during the amplification step, said primer forms a duplex with part of this region or with the entire region under the experimental conditions used, and that under those conditions said primer does not form a duplex with other regions of the polynucleic acids present in the sample to be analysed. It is to be understood that "duplex" as used hereby, means a duplex that will lead to specific amplification.

"Specific amplification" of a fragment of the HLA polynucleic acids means amplification of the fragment for which the primers were designed, and not of any other fragment of the polynucleic acids present in a sample.

The fact that amplification primers do not have to match exactly with the corresponding target sequence in the template to warrant proper amplification is amply documented in the literature (Kwok et al., 1990). However, when the primers are not completely complementary to their target sequence, it should be taken into account that the amplified fragments will have the sequence of the primers and not of the target sequence. Primers may be labelled with a label of choice (e.g. biotine). The amplification method used can be either polymerase chain reaction (PCR; Saiki et al., 1988), ligase chain reaction (LCR; Landgren et al., 1988; Wu and Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990) or amplification by means of Qβ replicase (Lomeli et al., 1989) or any other suitable method to amplify nucleic acid molecules known in the art.

Probe and primer sequences are represented throughout the specification as single stranded DNA oligonucleotides from the 5' to the 3' end. It is obvious to the man skilled in the art that any of the below-specified probes can be used as such, or in their complementary form, or in their RNA form (wherein T is replaced by U).

The probes according to the invention can be prepared by cloning of recombinant plasmids containing inserts including the corresponding nucleotide sequences, if need be by excision of the latter from the cloned plasmids by use of the adequate nucleases and recovering them, e.g. by fractionation according to molecular weight. The probes according to the present invention can also be synthesized chemically, for instance by the conventional phospho-triester method.

The oligonucleotides used as primers or probes may also comprise nucleotide analogues such as phosphorothiates (Matsukura et al., 1987), alkylphosphorothiates (Miller et al., 1979) or peptide nucleic acids (Nielsen et al., 1991; Nielsen et al., 1993) or may contain intercalating agents (Asseline et al., 1984). As most other variations or modifications introduced into the original DNA sequences of the invention these variations will necessitate adaptions with respect to the conditions under which the oligonucleotide should be used to obtain the required specificity and sensitivity. However the eventual results of hybridization will be essentially the same as those obtained with the unmodified oligonucleotides. The introduction of these modifications may be advantageous in order to positively influence characteristics such as hybridization kinetics, reversibility of the hybrid-formation, biological stability of the oligonucleotide molecules, etc. The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead) or a chip. Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labelled" refers to the use of labelled nucleic acids. Labelling may be carried out by the use of labelled nucleotides incorporated during the polymerase step of the amplification such as illustrated by Saiki et al. (1988) or Bej et al. (1990) or labelled primers, or by any other method known to the person skilled in the art. The nature of the label may be isotopic ($^{32}P$, $^{35}S$, etc.) or non-isotopic (biotin, digoxigenin, etc.).

The "biological sample" may be for instance blood, mouth swab or any other sample comprising genomic DNA.

For designing probes with desired characteristics, the following useful guidelines known to the person skilled in the art can be applied.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions are explained further herein.

\*\*The stability of the [probe:target] nucleic acid hybrid should be chosen to be compatible with the assay conditions. This may be accomplished by avoiding long AT-rich sequences, by terminating the hybrids with G:C base pairs, and by designing the probe with an appropriate Tm. The beginning and end points of the probe should be chosen so that the length and % GC result in a Tm about 2-10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be more stable at higher temperatures.

\*\*Conditions such as ionic strength and incubation temperature under which a probe will be used should also be taken into account when designing a probe. It is known that the degree of hybridization will increase as the ionic strength of the reaction mixture increases, and that the thermal stability of the hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10-50 bases in length occurs approximately 5° C. below the melting temperature for a given duplex. Incubation at temperatures below the optimum may allow mismatched base sequences to hybridize and can therefore result in reduced specificity.

\*\*It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the non-target nucleic acid.

\*\*Regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are available to search for this type of interaction. However, in certain instances, it may not be possible to avoid this type of interaction.

**Standard hybridization and wash conditions are disclosed in the Materials & Methods section of the Examples. Other conditions are for instance 3×SSC (Sodium Saline Citrate), 20% deionized FA (Formamide) at 50° C. Other solutions (SSPE (Sodium saline phosphate EDTA), TMAC (Tetramethyl ammonium Chloride), etc.) and temperatures can also be used provided that the specificity and sensitivity of the probes is maintained. When needed, slight modifications of the probes in length or in sequence have to be carried out to maintain the specificity and sensitivity required under the given circumstances.

The term "hybridization buffer" means a buffer allowing a hybridization reaction between the probes and the polynucleic acids present in the sample, or the amplified products, under the appropriate stringency conditions.

The term "wash solution" means a solution enabling washing of the hybrids formed under the appropriate stringency conditions.

FIGURE AND TABLE LEGENDS

FIG. 1 represents a drawing of the result of a LiPA experiment enabling typing of the HLA allele DRB1*0820. The numbers refer to probes of the DRB decoder 2nd generation kit (Innogenetics NV, Ghent, Belgium). The amplification and hybridization steps were performed as described in example 2.

Figure 2:
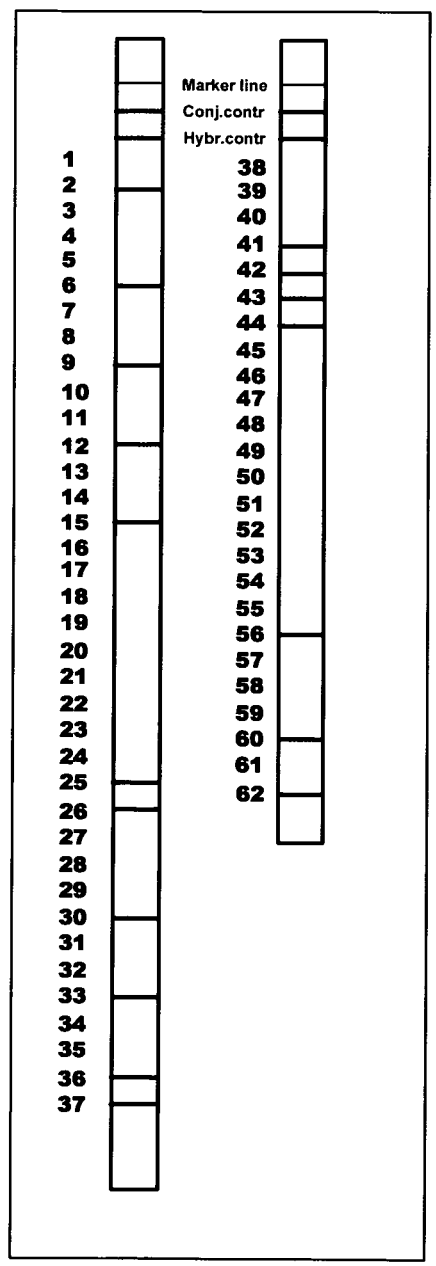

FIG. 2 represents a drawing of the result of a LiPA experiment enabling typing of the HLA allele DRB1*04new. The numbers refer to probes of the DRB decoder 2nd generation kit (Innogenetics NV, Ghent, Belgium). The amplification and hybridization steps were performed as described in example 4.

Figure 3:
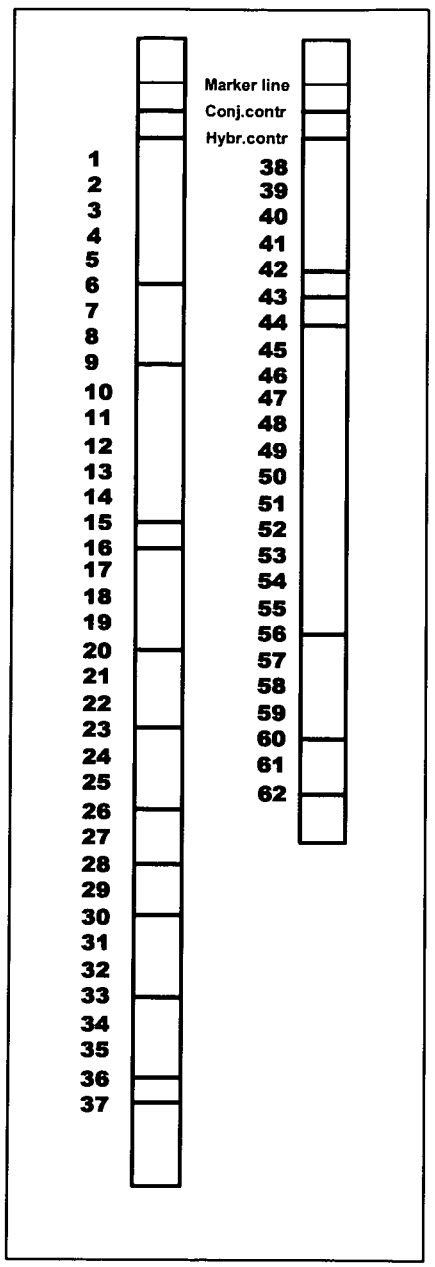

FIG. 3 represents a drawing of the result of a LiPA experiment enabling typing of the HLA allele DRB4*01new. The numbers refer to probes of the DRB decoder 2nd generation kit (Innogenetics NV, Ghent, Belgium). The amplification and hybridization steps were performed as described in example 6.

Figure 4:
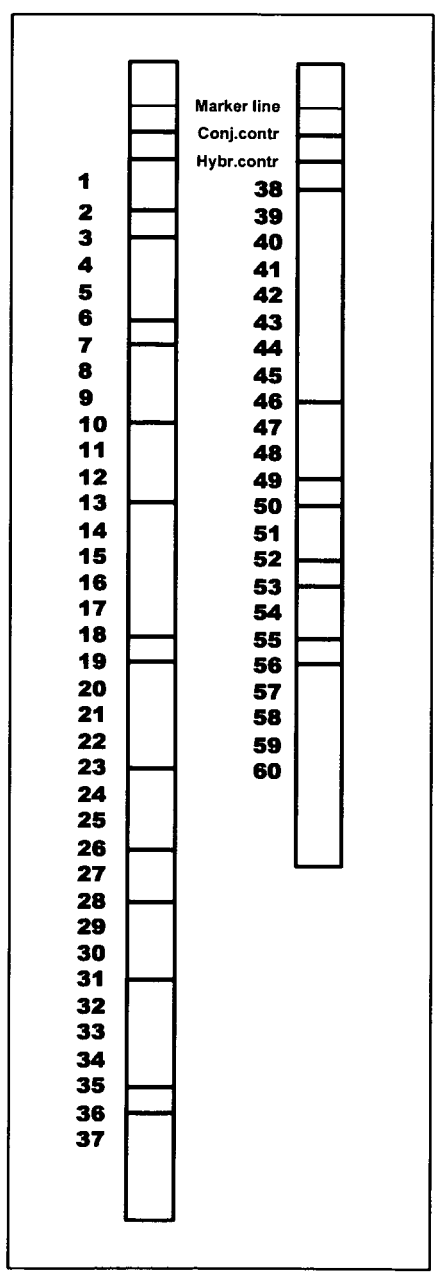

FIG. 4 represents a drawing of the result of a LiPA experiment enabling typing of the allele HLA-B*3913. The numbers refer to probes present in the LiPA HLA-B kit (Innogenetics NV, Ghent, Belgium). The experiment was performed as described in example 8.

Figure 5:
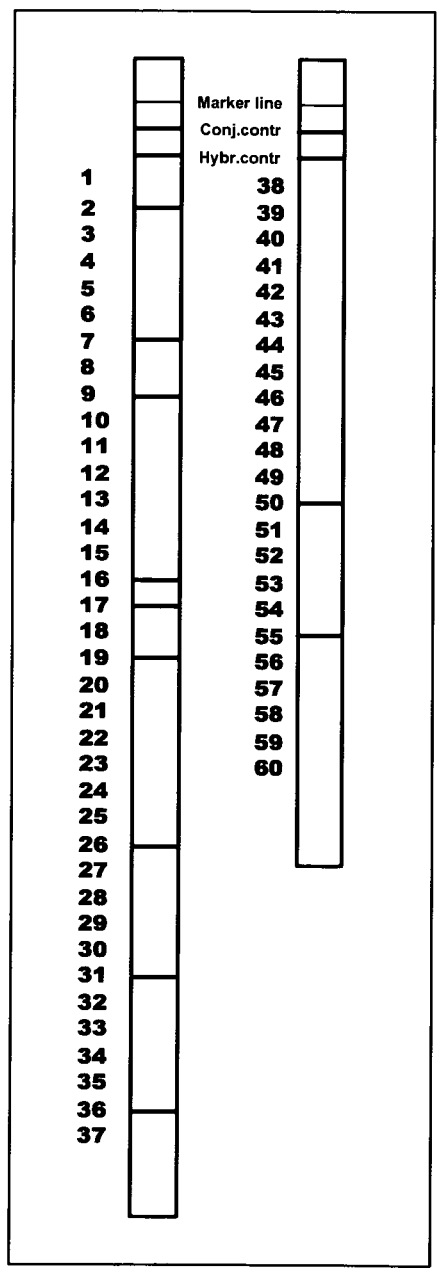

FIG. 5 represents a drawing of the result of a LiPA experiment enabling typing of the allele HLA-B*1406. The numbers refer to probes present in the LiPA HLA-B kit (Innogenetics NV, Ghent, Belgium). The experiment was performed as described in example 10.

Figure 6:
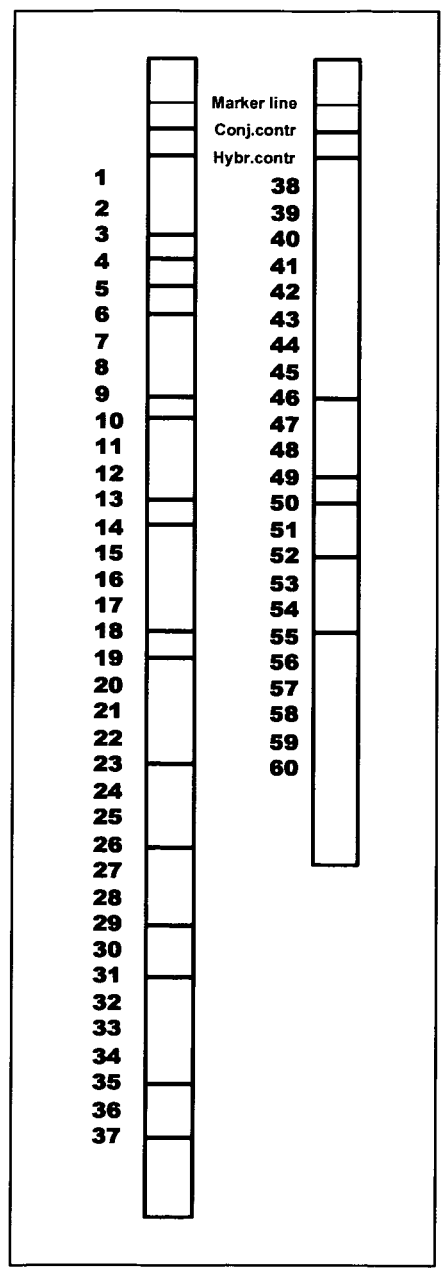

FIG. 6 represents a drawing of the result of a LiPA experiment enabling typing of the allele HLA-B*51new. The numbers refer to probes present in the LiPA HLA-B kit (Innogenetics NV, Ghent, Belgium). The experiment was performed as described in example 12.

Table 1. Primers used for the amplification of exon 2 of the HLA-allele DRB1*0820, the HLA-allele DRB1*04new and/or the HLA-allele DRB4*01new. The numbers before and after the sequences indicate the codons where the 5'-ends and the 3'-ends of the primers are located. "Intron" means that the 5'-end and/or the 3'-end is/are located in an intron.

Table 2. Oligonucleotide probes that can be used for typing of the HLA-allele DRB1*0820. The first column shows reference numbers for some of the probes. The sequences are given from 5' to 3'. The numbers before and after the sequences indicate the codons where the 5'-ends and the 3'-ends of the probes are located.

Table 3. Oligonucleotide probes that can be used for typing of the HLA-allele DRB1*04new. The first column shows reference numbers for the probes. The sequences are given from 5' to 3'. The numbers before and after the sequences indicate the codons where the 5'-ends and the 3'-ends of the probes are located.

Table 4. Oligonucleotide probes that can be used for typing of the HLA-allele DRB4*01new. The first column shows reference numbers for the probes. The sequences are given from 5' to 3'. The numbers before and after the sequences indicate the codons where the 5'-ends and the 3'-ends of the probes are located.

Table 5. Primers used for the amplification of exon2/exon 3 of the HLA-allele B*3913, the HLA-allele B*1406 and/or the HLA-allele B*51new.

Table 6. Oligonucleotide probes that can be used for typing of the HLA-allele B*3913. The first column shows reference numbers for some of the probes. The sequences are given from 5' to 3'.

Table 7. Oligonucleotide probes that can be used for typing of the HLA-allele B*1406. The first column shows reference numbers for the probes. The sequences are given from 5' to 3'.

Table 8. Oligonucleotide probes that can be used for typing of the HLA-allele B*51new. The first column shows reference numbers for the probes. The sequences are given from 5' to 3'.

EXAMPLES

Example 1

Sequence Determination of the Allele HLA-DRB1*0820

The allele DRB1*0820 was present in a blood sample from a Caucasian donor. The sample was collected by Dr. Bart Vandekerckhove of the Laboratorium Immunohematologie at the Bloedtransfusiecentrum Oost-Vlaanderen in Belgium. Polynucleic acids were prepared from the blood sample by use of the QIAamp Blood Kit (Qiagen, Hilden, Germany) according to the manufacturer's protocol. An amplification step was performed with the multiplex primer mix consisting of primers with SEQ ID NOs 4 to 9 as the 5'-primer and DRBP3'gen (SEQ ID NO 10) as the 3'-end primer. The PCR reaction cycle was composed of the following steps:

5 min at 95° C.

35 times (30 s at 95° C.; 20 s at 58° C.; 30 s at 72° C.)

10 min at 72° C.

The PCR reaction was carried out in 10 mM Tris.HCl pH 8.3; 50 mM KCl; 1.5 mM $MgCl_2$; 0.001% (w/v) gelatine; 200 µM dATP, dGTP, dCTP, dTTP (final concentrations) and 20 pmol of each primer and 1 U AmpliTaq (Applied Biosystems, Foster City, Calif., USA). Nucleotide sequence analysis was performed by use of an automated DNA sequencer Model 373A (Applied Biosystems, Foster City, Calif., USA) with fluorescence-labelled dideoxy nucleotides (Prism™ Ready Reaction Dye Terminator Cycle Sequencing Kit; Applied Biosystems, Foster City, Calif., USA). The primers used for the sequencing reaction were the same as for the amplification step. The following sequence, corresponding to exon 2 of the allele DRB1*0820 was obtained:

```
                                                  (SEQ ID NO 1)
CA CGT TTC TTG GAG TAC TCT ACG TCT GAG TGT CAT TTC

TTC AAT GGG ACG GAG CGG GTG CGG TTC CTG GAC AGA

TAC TTC TAT AAC CAA GAG GAG TAC GTG CGC TTC GAC

AGC GAC GTG GGG GAG TAC CGG GCG GTG ACG GAG CTG

GGG CGG CCT GAT GCC GAG TAC TGG AAC AGC CAG AAG

GAC TTC CTG GAA GAC AGG CGG GCC CTG GTG GAC ACC

TAC TGC AGA CAC AAC TAC GGG GTT GTG GAG AGC TTC

ACA GTG CAG CGG CGA
```

Example 2

Typing of the Allele DRB1*0820

The following method for typing of the allele DRB1*0820 in a sample is based on the LiPA technology (Stuyver et al, 1993). DNA is extracted from a blood sample with the QIAamp Blood Kit, as indicated in example 1. For the amplification step different primer mixes may be used: either a generic primer pair (such as SEQ ID NO 3 and SEQ ID NO 10), or a multiplex primer (such as the mix composed of primers with SEQ ID NO 4 to SEQ ID NO 9) combined with a generic primer (such as SEQ ID NO 10) or a generic primer combined with a primer encompassing the dimorphic codon 86 (such as SEQ ID NO 3 with SEQ ID NO 12). The amplification reaction is carried out in 10 mM Tris.HCl pH 8.3; 50 mM KCl; 1.5 mM $MgCl_2$; 0.001% (w/v) gelatine; 200 μM dATP, dGTP, dCTP, dTTP (final concentrations) and 20 pmol of each primer and 1 U AmpliTaq (Applied Biosystems, Foster City, Calif., USA). The PCR reaction is composed of 1 step of 5 min at 95° C., 35 cycles of three steps (30 s at 95° C., 20 s at 58° C., 30 s at 72° C.) and 1 step of 10 min at 72° C. The allele DRB1*0820 can subsequently be typed by a reverse hybridization step to a panel of oligonucleotide probes that are immobilized on a nitro-cellulose strip. A set of probes composed of the probes with SEQ ID NO 13 to SEQ ID NO 17 is sufficient to enable differentiation between the allele DRB1*0820 and any other presently known DRB1 allele at the allelic level. However, in clinical samples two different DRB1 alleles are present, which complicates the analysis and necessitates the use of a larger number of probes. Typing is even further complicated by the fact that also associated DRB alleles exist (DRB3, DRB4, DRB5), which show extensive sequence homology with the DRB1 alleles. In FIG. 1, for instance, an amplification reaction was carried out with the generic primers DRBp5'gen (SEQ ID NO 3) and DRBp3'gen (SEQ ID NO 10), under the conditions outlined above. The amplified product was subjected to a reverse hybridization assay, by use of the DRB decoder 2nd generation kit (Innogenetics NV, Ghent, Belgium) according to the manufacturer's protocol. This kit comprises a panel of 62 oligonucleotide probes, including the probes with SEQ ID NOs 13 to 17 of Table 2. FIG. 1 shows the result of the hybridization assay. The numbers indicate the different probes that are present on the strip. From this result it can be determined that the allele DRB1*0820 is present in the sample, in combination with the previously described alleles DRB1*04012 and the associated alleles DRB4*01011 and DRB4*0103. (These associated alleles have identical sequences in exon 2). The amplified nucleic acid fragment of allele DRB1*0820 hybridizes to the probes (lines) 9, 21, 25, 26 and 44 on the strip (corresponding to SEQ ID NOs 13, 16, 15, 14 and 17 respectively).

Example 3

Sequence Determination of the Allele HLA-DRB1*04new

The allele DRB1*04new was present in a blood sample from a Caucasian donor. The sample was collected by Dr. P. Jindra of the Hematologicko-onkologicke odd. in Plzen, Czech Republic. Polynucleic acids were prepared from the blood sample by use of the QIAamp Blood Kit (Qiagen, Hilden, Germany) according to the manufacturer's protocol.

In a first experiment, exon 2 was cloned in the pGEMt-vector (Promega, Madison, Wis., USA) after amplification with primer DRBp5'gen (SEQ ID NO 3) as the 5'-primer and DRBp3'gen (SEQ ID NO 10) as the 3'-primer. The PCR reaction cycle was composed of the following steps:

5 min at 95° C.
35 times (30 s at 95° C.; 20 s at 58° C.; 30 s at 72° C.)
10 min at 72° C.

The PCR reaction was carried out in 10 mM Tris.HCl pH 8.3; 50 mM KCl; 1.5 mM $MgCl_2$; 0.001% (w/v) gelatine; 200 μM dATP, dGTP, dCTP, dTTP (final concentrations) and 20 pmol of each primer and 1 U AmpliTaq (Applied Biosystems, Foster City, Calif., USA). Nucleotide sequence analysis was performed by use of an automated DNA sequencer Model 373A (Applied Bio systems, Foster City, Calif., USA) with fluorescence-labelled dideoxy nucleotides (Prism™ Ready Reaction Dye Terminator Cycle Sequencing Kit; Applied Biosystems, Foster City, Calif., USA). The primers used for the sequencing reaction were the SP6 and T7 primers provide by Eurogentec (Seraing, Belgium). The following sequence, corresponding to exon 2 of the allele DRB 1*04new was obtained:

```
                                                  (SEQ ID NO 68)
G ATC CTT CGT GTC CCC ACA GCA CGT TTC TTG GAG CAG

GTT AAA CCT GAG TGT CAT TTC TTC AAC GGG ACG GAG

CGG GTG CGG TTC CTG GAC AGA TAC TTC TAT CAC CAA

GAG GAG TAC GTG CGC TTC GAC AGC GAC GTG GGG GAG

TAC CGG GCG GTG ACG GAG CTG GGG CGG CCT GAT GCC

GAG TAC TGG AAC AGC CAG AAG GAC CTC CTG GAG CAG

AAG CGG GCC GCG GTG GAC ACC TAC TGC AGA CAC AAC

TAC GGG GTT GGT GAG AGC TTC ACA GTG CAG CGG CGA
```

The position of the generic primers used for the amplification of exon 2 is shown in bold.

In a second experiment, exon 2 was amplified with primer DRBp5'DR4 (SEQ ID NO 52) as the 5'-primer and DRBp3'gen (SEQ ID NO 10) as the 3'-primer. The PCR reaction cycle was composed of the following steps:

5 min at 95° C.
35 times (30 s at 95° C.; 20 s at 58° C.; 30 s at 72° C.)
10 min at 72° C.

The PCR reaction was carried out in 10 mM Tris.HCl pH 8.3; 50 mM KCl; 1.5 mM $MgCl_2$; 0.001% (w/v) gelatine; 200 μM dATP, dGTP, dCTP, dTTP (final concentrations) and 20 pmol of each primer and 1 U AmpliTaq (Applied Biosystems, Foster City, Calif., USA). Nucleotide sequence analysis was performed by use of an automated DNA sequencer Model 373A (Applied Biosystems, Foster City, Calif., USA) with fluorescence-labelled dideoxy nucleotides (Prism™ Ready Reaction Dye Terminator Cycle Sequencing Kit; Applied Biosystems, Foster City, Calif., USA). The primers used for the sequencing reaction were the same as for the amplification step. The following sequence, corresponding to exon 2 of the allele DRB1*04new was obtained:

(SEQ ID NO 69)
A CGT TTC TTG GAG CAG GTT AAA CCT GAG TGT CAT TTC

TTC AAC GGG ACG GAG CGG GTG CGG TTC CTG GAC AGA

TAC TTC TAT CAC CAA GAG GAG TAC GTG CGC TTC GAC

AGC GAC GTG GGG GAG TAC CGG GCG GTG ACG GAG CTG

GGG CGG CCT GAT GCC GAG TAC TGG AAC AGC CAG AAG

GAC CTC CTG GAG CAG AAG CGG GCC GCG GTG GAC ACC

TAC TGC AGA CAC AAC TAC GGG GTT GGT GAG AGC TTC

ACA GTG CAG CGG CGA

The position of the primers used for the amplification of exon 2 is shown in bold.

Example 4

Typing of the Allele DRB1*04new

The following method for typing of the allele DRB1*04new in a sample is based on the LiPA technology (Stuyver et al, 1993). DNA is extracted from a blood sample with the QIAamp Blood Kit, as indicated in example 3. For the amplification step different primer mixes may be used: either a generic primer pair (such as SEQ ID NO 3 and SEQ ID NO 10), or a multiplex primer (such as the mix composed of primers with SEQ ID NO 4 to SEQ ID NO 9 or the mix composed of primers with SEQ ID NOs 4, 5, 52, 7, 8 and 9) combined with a generic primer (such as SEQ ID NO 10) or a generic primer combined with a primer encompassing the dimorphic codon 86 (such as SEQ ID NO 3 with SEQ ID NO 12). The amplification reaction is carried out in 10 mM Tris.HCl pH 8.3; 50 mM KCl; 1.5 mM MgCl$_2$; 0.001% (w/v) gelatine; 200 µM dATP, dGTP, dCTP, dTTP (final concentrations) and 20 pmol of each primer and 1 U AmpliTaq (Applied Biosystems, Foster City, Calif., USA). The PCR reaction is composed of 1 step of 5 min at 95° C., 35 cycles of three steps (30 s at 95° C., 20 s at 58° C., 30 s at 72° C.) and 1 step of 10 min at 72° C. The allele DRB1*04new can subsequently be typed by a reverse hybridization step to a panel of oligonucleotide probes that are immobilized on a nitro-cellulose strip. A set of probes composed of the probes with SEQ ID NO 55 to SEQ ID NO 61 is sufficient to enable differentiation between the allele DRB1*04new and any other presently known DRB1 allele at the allelic level. However, in clinical samples two different DRB1 alleles are present, which complicates the analysis and necessitates the use of a larger number of probes. Typing is even further complicated by the fact that also associated DRB alleles exist (DRB3, DRB4, DRB5), which show extensive sequence homology with the DRB1 alleles. In FIG. 2, for instance, an amplification reaction was carried out with the generic primers DRBp5'gen (SEQ ID NO 3) and DRBp3'gen (SEQ ID NO 10), under the conditions outlined above. The amplified product was subjected to a reverse hybridization assay, by use of the DRB decoder 2nd generation kit (Innogenetics NV, Ghent, Belgium) according to the manufacturer's protocol. This kit comprises a panel of 62 oligonucleotide probes, including the probes with SEQ ID NOs 55 to 61 of Table 3. FIG. 2 shows the result of the hybridization assay. The numbers indicate the different probes that are present on the strip. From this result it can be determined that the allele DRB1*04new (lines 12, 26, 36, 37, 42, 43, 56) is present in the sample, in combination with the previously described alleles DRB1*1104 (lines 2, 9, 25, 30, 33, 44, 56) and two of the associated alleles DRB4*01011 (lines 15, 36, 41, 44, 60, 62) and DRB3*0202 (lines 6, 26, 36, 43, 60). The amplified nucleic acid fragment of allele DRB1*04new hybridizes to the probes (lines) 12, 26, 36, 37, 42, 43 and 56 on the strip (corresponding to SEQ ID NOs 55, 58, 60, 61, 56, 57 and 59 respectively).

Example 5

Sequence Determination of the Allele HLA-DRB4*01new

The allele DRB4*01new was present in a blood sample from a Caucasian donor. The sample was collected by Dr. Bohuslava Jilkova of the HLA-Laboratory in Hradec Kralove, Czech Republic. Polynucleic acids were prepared from the blood sample by use of the QIAamp Blood Kit (Qiagen, Hilden, Germany) according to the manufacturer's protocol.

In a first experiment, exon 2 was cloned in the pGEMt-vector (Promega, Madison, Wis., USA) after amplification with primer DRBp5'intron (SEQ ID NO 53) as the 5'-primer and DRBp3'intron (SEQ ID NO 107) as the 3'-primer. The PCR reaction cycle was composed of the following steps:
5 min at 95° C.
35 times (30 s at 95° C.; 20 s at 58° C.; 30 s at 72° C.)
10 min at 72° C.

The PCR reaction was carried out in 10 mM Tris.HCl pH 8.3; 50 mM KCl; 1.5 mM MgCl$_2$; 0.001% (w/v) gelatine; 200 µM dATP, dGTP, dCTP, dTTP (final concentrations) and 20 pmol of each primer and 1 U AmpliTaq (Applied Biosystems, Foster City, Calif., USA). Nucleotide sequence analysis was performed by use of an automated DNA sequencer Model 373A (Applied Biosystems, Foster City, Calif., USA) with fluorescence-labelled dideoxy nucleotides (Prism™ Ready Reaction Dye Terminator Cycle Sequencing Kit; Applied Biosystems, Foster City, Calif., USA). The primers used for the sequencing reaction were the SP6 and T7 primers provide by Eurogentec (Seraing, Belgium). The following sequence, corresponding to exon 2 of the allele DRB4*01new was obtained:

(SEQ ID NO 70)
AC CGG ATC CTT CGT GTC CCC ACA GCA CGT TTC TTG GAG

CAG GCT AAG TGT GAG TGT CAT TTC CTC AAT GGG ACG

GAG CGA GTG TGG AAC CTG ATC AGA TAC ATC TAT AAC

CAA GAG GAG TAC GCG CGC TAC AAC AGT GAT CTG GGG

GAG TAC CAG GCG GTG ACG GAG CTG GGG CGG CCT GAC

GCT GAG TAC TGG AAC AGC CAG AAG GAC CTC CTG GAG

CGG AGG CGG GCC GAG GTG GAC ACC TAC TGC AGA TAC

AAC TAC GGG GTT GTG GAG AGC TTC ACA GTG CAG CGG

CGA GGT GAG CAT GGT GGA GGG CGG G

The position of the primers used for the amplification of exon 2 is shown in bold.

In a second experiment, exon 2 was amplified with primer DRB4p5' (SEQ ID NO 54) as the 5'-primer and DRBp3'gen (SEQ ID NO 10) as the 3'-primer. The PCR reaction cycle was composed of the following steps:

5 min at 95° C.
35 times (30 s at 95° C.; 20 s at 58° C.; 30 s at 72° C.)
10 min at 72° C.

The PCR reaction was carried out in 10 mM Tris.HCl pH 8.3; 50 mM KCl; 1.5 mM MgCl$_2$; 0.001% (w/v) gelatine; 200 μM dATP, dGTP, dCTP, dTTP (final concentrations) and 20 pmol of each primer and 1 U AmpliTaq (Applied Biosystems, Foster City, Calif., USA). Nucleotide sequence analysis was performed by use of an automated DNA sequencer Model 373A (Applied Biosystems, Foster City, Calif., USA) with fluorescence-labelled dideoxy nucleotides (Prism™ Ready Reaction Dye Terminator Cycle Sequencing Kit; Applied Biosystems, Foster City, Calif., USA). The primers used for the sequencing reaction were the same as for the amplification step. The following sequence, corresponding to exon 2 of the allele DRB1*04new was obtained:

```
                                              (SEQ ID NO 71)
TAA GTG TGA GTG TCA TTT CCT CAA TGG GAC GGA GCG

AGT GTG GAA CCT GAT CAG ATA CAT CTA TAA CCA AGA

GGA GTA CGC GCG CTA CAA CAG TGA TCT GGG GGA GTA

CCA GGC GGT GAC GGA GCT GGG GCG GCC TGA CGC TGA

GTA CTG GAA CAG CCA GAA GGA CCT CCT GGA GCG GAG

GCG GGC CGA GGT GGA CAC CTA CTG CAG ATC AAC TAC

GGG GTT GTG GAG AGC TTC ACA GTG CAG CGG CGA
```

The position of the primers used for the amplification of exon 2 is shown in bold.

Example 6

Typing of the Allele DRB4*01new

The following method for typing of the allele DRB4*01new in a sample is based on the LiPA technology (Stuyver et al, 1993). DNA is extracted from a blood sample with the QIAamp Blood Kit, as indicated in example 5. For the amplification step different combinations of 5' and 3' primers can be used: for example, either a generic primer pair (such as SEQ ID NO 3 and SEQ ID NO 10 or SEQ ID NO 53 and SEQ ID NO 107), or a specific primer, such as SEQ ID NO 54, possibly in a mix composed of other 5' primers used for the amplification of different DRB alleles (e.g. SEQ ID NO 4 to 9) combined with a generic primer (such as SEQ ID NO 10 or 107) or a generic primer combined with a primer encompassing the dimorphic codon 86 (such as SEQ ID NO 3 with SEQ ID NO 12). The amplification reaction is carried out in 10 mM Tris.HCl pH 8.3; 50 mM KCl; 1.5 mM MgCl$_2$; 0.001% (w/v) gelatine; 200 μM dATP, dGTP, dCTP, dTTP (final concentrations) and 20 pmol of each primer and 1 U AmpliTaq (Applied Biosystems, Foster City, Calif., USA). The PCR reaction is composed of 1 step of 5 min at 95° C., 35 cycles of three steps (30 s at 95° C., 20 s at 58° C., 30 s at 72° C.) and 1 step of 10 min at 72° C. The allele DRB4*01new can subsequently be typed by a reverse hybridization step to a panel of oligonucleotide probes that are immobilized on a nitro-cellulose strip. A set of probes composed of the probes with SEQ ID NO 62 to SEQ ID NO 66 is sufficient to enable differentiation between the allele DRB4*01new and any other presently known DRB4 allele at the allelic level. Typing is even further complicated by the fact that also DRB 1 alleles and other associated alleles exist (DRB3, DRB4, DRB5), which show extensive sequence homology with the DRB4 alleles. This complicates the analysis and necessitates the use of a larger number of probes. In FIG. 3, for instance, an amplification reaction was carried out with the generic primers DRBp5' gen (SEQ ID NO 3) and DRBp3' gen (SEQ ID NO 10), under the conditions outlined above. The amplified product was subjected to a reverse hybridization assay, by use of the DRB decoder 2nd generation kit (Innogenetics NV, Ghent, Belgium) according to the manufacturer's protocol. This kit comprises a panel of 62 oligonucleotide probes, including the probes with SEQ ID NOs 62 to 66 of Table 4. FIG. 3 shows the result of the hybridization assay. The numbers indicate the different probes that are present on the strip. From this result it can be determined that the allele DRB4*01new is present in the sample, in combination with the previously described alleles DRB1*0403 (lines 15, 20, 26, 36, 37, 42, 44), DRB1*1301 (lines 9, 16, 23, 26, 28, 30, 44, 56) and DRB3*0206 (lines 6, 26, 36, 43). The amplified nucleic acid fragment of allele DRB4*01new hybridizes to the probes (lines) 15, 36, 44, 60 and 62 on the strip (corresponding to SEQ ID NOs 62, 63, 64, 65 and 66 respectively).

Example 7

Sequence Determination of the Allele HLA-B*3913

The allele B*3913 was present in a blood sample from a Brazilian Caucasian donor. The sample was collected by Dr. M E Moraes of the Lab de Immunogenética, HSE/INCA, Rio De Janeiro, Brazil. Polynucleic acids were prepared from the blood sample by use of the QIAamp Blood Kit (Qiagen, Hilden, Germany) according to the manufacturer's protocol. An amplification step was performed with primers IBPIN1 and IBPIN3. The PCR reaction consisted of the following steps:

1 min at 96° C.
5 times (30 s at 95° C.; 50 s at 64° C.; 50 s at 72° C.)
5 times (30 s at 95° C.; 50 s at 62° C.; 50 s at 72° C.)
10 times (30 s at 95° C.; 50 s at 60° C.; 50 s at 72° C.)
15 times (30 s at 95° C.; 50 s at 55° C.; 50 s at 72° C.)
10 min at 72° C.

The amplification reaction was carried out in 50 mM Tris-HCl pH 9.2, 16 mM (NH$_4$)$_2$SO$_4$, 200 μM dNTPs, 2.5 U Taq polymerase, 1.5 mM MgCl$_2$, 15 pmole of each primer and 0.1 to 0.5 μg DNA. Nucleotide sequence analysis was performed by use of an automated DNA sequencer Model 373A (Applied Biosystems, Foster City, Calif., USA) with fluorescence-labelled dideoxy nucleotides (Prism™ Ready Reaction Dye Terminator Cycle Sequencing Kit; Applied Biosystems, Foster City, Calif., USA). The primers used for the sequencing reaction were the same as for the amplification step. The following sequences, corresponding to exon 2 and exon 3 of the allele B*3913 were obtained:

```
                                                          (SEQ ID NO 22)
GCTCCCACTCCATGAGGTATTTCTACACCTCCGTGTCCCGGCCCGGCCGCGGGGAGCCCCGC

TTCATCTCAGTGGGCTACGTGGACGACACGCAGTTCGTGAGGTTCGACAGCGACGCCGCGAG

TCCGAGAGAGGAGCCGCGGGCGCCGTGGATAGAGCAGGAGGGGCCGGAGTATTGGGACCGGG

AGACACAGATCTCCAAGACCAACACACAGACTTACCGAGAGAGCCTGCGGAACCTGCGCGGC

TACTACAACCAGAGCGAGGCCG exon 2
                                                          (SEQ ID NO 23)
GGTCTCACACCCTCCAGAGGATGTACGGCTGCGACGTGGGGCCGGACGGGCGCCTCCTCCGC

GGGCATAACCAGTTCGCCTACGACGGCAAGGATTACATCGCCCTGAACGAGGACCTGAGCTC

CTGGACCGCGGCGGACACCGCGGCTCAGATCACCCAGCGCAAGTGGGAGGCGGCCCGTGTGG

CGGAGCAGCTGAGAACCTACCTGGAGGGCACGTGCGTGGAGTGGCTCCGCAGATACCTGGAG

AACGGGAAGGAGACGCTGCAGCGCGCGG exon 3
```

Example 8

Typing of the Allele B*3913

The following method, that may be used to type the allele B*3913 in a sample, is based on the LiPA technology (Stuyver et al, 1993). Nucleic acids are extracted from a blood sample with the QIAamp Blood Kit, as indicated in example 7. For the amplification step the primer pair IBPIN1 (SEQ ID NO 26) and IBPIN3 (SEQ ID NO 27) is used. The PCR reaction is performed under the same conditions as in example 7. The allele HLA-B*3913 can subsequently be typed by a reverse hybridization step to a panel of oligonucleotide probes that are immobilized on a nitro-cellulose strip. For instance, FIG. 4 shows the result of a reverse hybidization assay according to the LiPA technique. After an amplification step as described above, the amplified nucleic acids were hybridized to a panel of 60 probes by use of the LiPA HLA-B kit (Innogenetics NV, Ghent, Belgium) according to the manufacturer's protocol. From the result shown in FIG. 4, it can be derived that the sample contained the allele HLA-B*3913, in combination with the known allele HLA-B*52012. The numbers in FIG. 4 indicate probes that are present on the strip (note that these probes are not the same probes as those in FIGS. 1-3). The amplified nucleic acid fragment of allele HLA-B*3913 hybridizes to the following probes (lines) on the strip: 2 (SEQ ID NO 30), 7 (SEQ ID NO 32), 10 (SEQ ID NO 34), 13 (SEQ ID NO 35), 18 (SEQ ID NO 36), 19 (SEQ ID NO 37), 26 (SEQ ID NO 39), 28 (SEQ ID NO 42), 36 (SEQ ID NO 47), 38 (SEQ ID NO 45), 50 (SEQ ID NO 38), 53 (SEQ ID NO 43) and 56 (SEQ ID NO 28).

Example 9

Sequence Determination of the Allele HLA-B*1406

The allele B*1406 was present in a blood sample from a Belgian Caucasian donor. The sample was collected by Dr. M P Emonds of the Bloodtransfusion Center, Leuven, Belgium. Polynucleic acids were prepared from the blood sample by use of the QIAamp Blood Kit (Qiagen, Hilden, Germany) according to the manufacturer's protocol. An amplification step was performed with primers IBPIN1 and IBPIN3. The PCR reaction consisted of the following steps:
1 min at 96° C.
5 times (30 s at 95° C.; 50 s at 64° C.; 50 s at 72° C.)
5 times (30 s at 95° C.; 50 s at 62° C.; 50 s at 72° C.)
10 times (30 s at 95° C.; 50 s at 60° C.; 50 s at 72° C.)
15 times (30 s at 95° C.; 50 s at 55° C.; 50 s at 72° C.)
10 min at 72° C.

The amplification reaction was carried out in 50 mM Tris-HCl pH 9.2, 16 mM $(NH_4)_2SO_4$, 200 µM dNTPs, 2.5 U Taq polymerase, 1.5 mM $MgCl_2$, 15 pmole of each primer and 0.1 to 0.5 µg DNA. Nucleotide sequence analysis was performed by use of an automated DNA sequencer Model 373A (Applied Biosystems, Foster City, Calif., USA) with fluorescence-labelled dideoxy nucleotides (Prism™ Ready Reaction Dye Terminator Cycle Sequencing Kit; Applied Biosystems, Foster City, Calif., USA). The primers used for the sequencing reaction were the same as for the amplification step. The following sequences, corresponding to exon 2 and exon 3 of the allele B*1406 were obtained:

```
                                                          (SEQ ID NO 72)
GCTCCCACTCCATGAGGTATTTCTACACCGCCGTGTCCCGGCCCGGCCGC

GGGGAGCCCCGCTTCATCTCAGTGGGCTACGTGGACGACACGCAGTTCGT

GAGGTTCGACAGCGACGCCGCGAGTCCGAGAGAGGAGCCGCGGGCGCCGT

GGATAGAGCAGGAGGGGCCGGAATATTGGGACCGGAACACACAGATCTGC

AAGACCAACACACAGACTGACCGAGAGAGCCTGCGGAACCTGCGCGGCTA

CTACAACCAGAGCGAGGCCG exon 2
                                                          (SEQ ID NO 73)
GGTCTCACACCCTCCAGAGGATGTACGGCTGCGACGTGGGGCCGGACGGG

CGCCTCCTCCGCGGGTATAACCAGTTCGCCTACGACGGCAAGGATTACAT

CGCCCTGAACGAGGACCTGAGCTCCTGGACCGCGGCGGACACCGCGGCTC

AGATCACCCAGCGCAAGTGGGAGGCGGCCCGTGAGGCGGAGCAGCTGAGA

GCCTACCTGGAGGGCACGTGCGTGGAGTGGCTCCGCAGACACCTGGAGAA

CGGGAAGGAGACGCTGCAGCGCGCGG exon 3
```

Example 10

Typing of the Allele B*1406

The following method, that may be used to type the allele B*1406 in a sample, is based on the LiPA technology (Stuyver et al, 1993). Nucleic acids are extracted from a blood sample with the QIAamp Blood Kit, as indicated in example 9. For the amplification step the primer pair IBPIN1 (SEQ ID NO 26) and IBPIN3 (SEQ ID NO 27) is used. The PCR reaction is performed under the same conditions as in example 9. The allele HLA-B*1406 can subsequently be typed by a reverse hybridization step to a panel of oligonucleotide probes that are immobilized on a nitro-cellulose strip. For instance, FIG. 5 shows the result of a reverse hybidization assay according to the LiPA technique. After an amplification step as described above, the amplified nucleic acids were hybridized to a panel of 60 probes by use of the LiPA HLA-B kit (Innogenetics NV, Ghent, Belgium) according to the manufacturer's protocol. From the result shown in FIG. 5, it can be derived that the sample contained the allele HLA-B*1406. The numbers in FIG. 5 indicate probes that are present on the strip (note that these probes are not the same probes as those in FIGS. 1-3). The amplified nucleic acid fragment of allele HLA-B*1406 hybridizes to the following probes (lines) on the strip: 2 (SEQ ID NO 30), 7 (SEQ ID NO 32), 9 (SEQ ID NO 79), 16 (SEQ ID NO 80), 17 (SEQ ID NO 81), 19 (SEQ ID NO 37), 26 (SEQ ID NO 83), 31 (SEQ ID NO 87), 36 (SEQ ID NO 47), 50 (SEQ ID NO 82) and 55 (SEQ ID NO 89).

Example 11

Sequence Determination of the Allele HLA-B*51new

The allele B*51new was present in a blood sample from a Brazilian Caucasian donor. The sample was collected by Dr. M E Moraes of the Lab de Immunogenética, HSE/INCA, Rio De Janeiro, Brazil. Polynucleic acids were prepared from the blood sample by use of the QIAamp Blood Kit (Qiagen, Hilden, Germany) according to the manufacturer's protocol. An amplification step was performed with primers IBPIN1 and IBPIN3. The PCR reaction consisted of the following steps:

1 min at 96° C.
5 times (30 s at 95° C.; 50 s at 64° C.; 50 s at 72° C.)
5 times (30 s at 95° C.; 50 s at 62° C.; 50 s at 72° C.)
10 times (30 s at 95° C.; 50 s at 60° C.; 50 s at 72° C.)
15 times (30 s at 95° C.; 50 s at 55° C.; 50 s at 72° C.)
10 min at 72° C.

The amplification reaction was carried out in 50 mM Tris-HCl pH 9.2, 16 mM $(NH_4)_2SO_4$, 200 µM dNTPs, 2.5 U Taq polymerase, 1.5 mM $MgCl_2$, 15 pmole of each primer and 0.1 to 0.5 µg DNA. Nucleotide sequence analysis was performed by use of an automated DNA sequencer Model 373A (Applied Biosystems, Foster City, Calif., USA) with fluorescence-labelled dideoxy nucleotides (Prism™ Ready Reaction Dye Terminator Cycle Sequencing Kit; Applied Biosystems, Foster City, Calif., USA). The primers used for the sequencing reaction were the same as for the amplification step. The following sequences, corresponding to exon 2 and exon 3 of the allele B*51new were obtained:

(SEQ ID NO 74)
GCTCCCACTCCATGAGGTATTTCTACACCGCCGTGTCCCGGCCCGGCCGC

GGGGAGCCCCGCTTCATCTCAGTGGGCTACGTGGACGACACGCAGTTCGT

GAGGTTCGACAGCGACGCCGCGAGTCCGAGAGAGGAGCCGCGGGCGCCGT

GGATAGAGCAGGAGGGGCCGGAATATTGGGACCGGAACACACAGATCTGC

-continued
AAGACCAACACACAGACTGACCGAGAGAGCCTGCGGAACCTGCGCGGCTA

CTACAACCAGAGCGAGGCCG exon 2

(SEQ ID NO 75)
GGTCTCACACCCTCCAGAGGATGTACGGCTGCGACGTGGGGCCGGACGGG

CGCCTCCTCCGCGGGTATAACCAGTTCGCCTACGACGGCAAGGATTACAT

CGCCCTGAACGAGGACCTGAGCTCCTGGACCGCGGCGGACACCGCGGCTC

AGATCACCCAGCGCAAGTGGGAGGCGGCCCGTGAGGCGGAGCAGCTGAGA

GCCTACCTGGAGGGCACGTGCGTGGAGTGGCTCCGCAGACACCTGGAGAA

CGGGAAGGAGACGCTGCAGCGCGCGG exon 3

Example 12

Typing of the Allele B*51new

The following method, that may be used to type the allele B*1406 in a sample, is based on the LiPA technology (Stuyver et al, 1993). Nucleic acids are extracted from a blood sample with the QIAamp Blood Kit, as indicated in example 11. For the amplification step the primer pair IBPIN1 (SEQ ID NO 26) and IBPIN3 (SEQ ID NO 27) is used. The PCR reaction is performed under the same conditions as in example 11. The allele HLA-B*51new can subsequently be typed by a reverse hybridization step to a panel of oligonucleotide probes that are immobilized on a nitro-cellulose strip. For instance, FIG. 6 shows the result of a reverse hybidization assay according to the LiPA technique. After an amplification step as described above, the amplified nucleic acids were hybridized to a panel of 60 probes by use of the LiPA HLA-B kit (Innogenetics NV, Ghent, Belgium) according to the manufacturer's protocol. From the result shown in FIG. 6, it can be derived that the sample contained the allele HLA-B*51new, in combination with the known allele HLA-B*1501. The numbers in FIG. 6 indicate probes that are present on the strip (note that these probes are not the same probes as those in FIGS. 1-3). The amplified nucleic acid fragment of allele HLA-B*51new hybridizes to the following probes (lines) on the strip: 3 (SEQ ID NO 90), 6 (SEQ ID NO 91), 9 (SEQ ID NO 79), 14 (SEQ ID NO 92), 18 (SEQ ID NO 93), 23 (SEQ ID NO 98), 31 (SEQ ID NO 87), 35 (SEQ ID NO 99), 46 (SEQ ID NO 94), 49 (SEQ ID NO 95), 52 (SEQ ID NO 100), 55 (SEQ ID NO 89).

REFERENCES

Andersson G, Larhammar D, Widmark E, Servenius B, Peterson P A and Rask L (1987) Class II genes of the human major histocompatibility complex. Organization and evolutionary relationship of the DRbeta genes. J. Biol. Chem 262:8748-8758.

Apple R J and Erlich H A (1996) HLA classII genes: structure and diversity. Chapter 5 HLA and MHC: genes, molecules and function. BIOS Scientific Publishers Ltd., Oxford, UK.

Asseline U, Delarue M, Lancelot G, Toulme F and Thuong N (1984) Nucleic acid-binding molecules with high affinity and base sequence specificity: intercalating agents covalently linked to oligodeoxynucleotides. Proc. Natl. Acad. Sci. USA 81:3297-3301.

Barany F (1991) The ligase chain reaction in a PCR world. PCR Methods Appl. 1:5-16.

Bej A, Mahbubani M, Miller R, Di Cesare J, Haff L and Atlas R (1990) Multiplex PCR amplification and immobilized capture probes for detection of bacterial pathogens and indicators in water. Mol. Cell Probes 4:353-365.

Campbell R D and Trowsdale J (1993) Map of the human MHC. Immunology Today 14:349-352.

Clay T M, Culpan D, Howell W M, Sage D A, Bradley B A and Bidwell J L (1994) UHG crossmatching. A comparison with PCR-SSO typing in the selection of HLA-DPB-compatible bone marrow donors. Transplantation 58: 200-207.

Compton J (1991) Nucleic acid sequence-based amplification. Nature 350: 91-92.

Duck P (1990) Probe amplifier system based on chimeric cycling oligonucleotides. Biotechniques 9: 142-147.

Guatelli J, Whitfield K, Kwoh D, Barringer K, Richman D and Gengeras T (1990) Isothermal, in vitro amplification of nucleic acids by a multienzyme reaction modeled after retroviral replication. Proc. Natl. Acad. Sci. USA 87: 1874-1878.

Hirschorn K, Bach F, Kolodny R L and Firschen I L (1963) Immune response and mitotis of human peripheral blood lymphocytes in vitro. Science 142: 1185-1187.

Kissmeyer N F, Svejgaard A and Hauge M (1969) The HLA system defined with lymphocytoyoxic and platelet antibodies in relation to kidney transplantation. Transplant. Proc. 1: 357-361.

Kwoh D, Davis G, Whitfield K, Chappelle H, Dimichele L and Gingeras T (1989) Transcription-based amplification system and detection of amplified human immunodeficiency virus type 1 with a bead-based sandwich hybridization format. Proc. Natl. Acad. Sci. USA 86: 1173-1177.

Kwok S, Kellogg D, McKinney N, Spasic D, Goda L, Levenson C and Sinisky J (1990) Effects of primer-template mismatches on the polymerase chain reaction: Human immunodeficiency virus type 1 model studies. Nucl. Acids Res. 18: 999-1005.

Landgren U, Kaiser R, Sanders J and Hood L (1988) A ligase-mediated gene detection technique. Science 241:1077-1080.

Lomeli H, Tyagi S, Pritchard C, Lisardi P and Kramer F (1989) Quantitative assays based on the use of replicatable hybridization probes. Clin. Chem. 35: 1826-1831.

Matsukura M, Shinozuka K, Zon G, Mitsuya H, Reitz M, Cohen J and Broder S (1987) Phosphorothioate analogs of oligodeoxynucleotides: inhibitors of replication and cytopathic effects of human immunodeficiency virus. Proc. Natl. Acad. Sci. USA 84: 7706-7710.

Miller P, Yano J, Yano E, Carroll C, Jayaram K and Ts'o P (1979) Nonionic nucleic acid analogues. Synthesis and characterization of dideoxyribonucleoside methylphosphonates. Biochemistry 18: 5134-5143.

Mullis K, Faloona F, Scharf S, Saiki R, Horn G and Erlich H (1986) Specific enzymatic amplification of DNA in vitro: the polymerase chain reaction. Gold Spring Harb. Symp. Quant. Biol. 1: 263-273.

Mullis K B and Faloona F A (1987) Specific synthesis of DNA in vitro via a polymerase-catalyzed chain reaction. Methods Enzymol. 155: 335-350.

Nielsen P, Egholm M, Berg R and Buchardt O (1991) Sequence-selective recognition of DNA by strand displacement with a thymine-substituted polyamide. Science 254:1497-1500.

Nielsen P, Egholm M, Berg R, Buchardt O (1993) Sequence specific inhibition of DNA restriction enzyme cleavage by PNA. Nucleic-Acids-Res. 21:197-200.

Olerup O and Zetterquist H (1991) HLA-DRB1*01 subtyping by allele-specific PCR amplification: a sensitive, specific and rapid technique. Tissue Antigens 37: 197-204.

Saiki R K, Bugawan T L, Horn G, TMullis K B and Erlich H A (1986) Analysis of enzymatically amplified beta-globin and HLA-DQ alpha DNA with allele-specific oligonucleotide probes. Nature 324: 163-166.

Saiki R K, Gelfand D H, Stoffel S, Scharf S J, Higuchi R, Horn G T, Mullis K B and Erlich H A (1988) Primer directed enzymatic amplification of DNA with a thermostable DNA polymerase. Science 239: 487-491.

Saiki R K, Walsh P S, Levenson C H and Erlich H A (1989) Genetic analysis of amplified DNA with immobilizes sequence-specific oligonucleotide probes. Proc. Natl. Acad. Sci. USA 86: 6230-6234.

Sambrook J, Fritsch E, Maniatis T (1989) Molecular cloning: a laboratory manual. Cold Spring Harbor Laboratory Press, Cold Spring Harbor, N.Y., USA.

Santamaria P, Boyce-Jacino M T, Lindstrom A L, Barbosa J J, Faras A J and Rich S S (1992) HLA class II "typing": direct sequencing of DRB, DQB and DQA genes. Hum. Immunol. 33: 69-81.

Santamaria P, Lindstrom A L, Boyce J M, Jacino M T, Myster S H, Barbosa J J, Faras A J and Rich S S (1993) HLA class I sequence-based typing. Hum. Immunol. 37: 39-50.

Spencer W R and Parham P (1996) HLA class I genes: structure and diversity. Chapter 4. HLA and MHC: genes, molecules and function. BIOS Scientific Publishers Ltd., Oxford, UK.

Stuyver L, Rossau R, Wyseur A, Duhamel M, Vanderborght B, Van Heuverswyn H and Maertens G (1993) Typing of hepatitis C virus isolates and characterization of new subtypes using a line probe assay. J. Gen. Virol. 74: 1093-1102.

Terasaki P H and McClelland J D (1964) Microdoplet assay of human serum cytotoxins. Nature 204: 998-1007.

Townsend A and Bodmer H (1989) Antigen recognition by Class I-restricted T lymphocytes. Annu. Rev. Immunol. 7: 601-624.

Wu D and Wallace B (1989) The ligation amplification reaction (LAR)—amplification of specific DNA sequences using sequential rounds of template-dependent ligation. Genomics 4: 560-569.

Yang S Y (1987) A standardised method for detection of HLA-A and HLA-B alleles by one-dimensional isoelectric focusing (IEF) gel electrophoresis. Immunobiology of HLA. Histocompatibility testing (ed. B Dupont). Springer-Verlag, New York, USA. pp. 332-335.

Yoshida M, Kimura A, Numano F and Sasazuki T (1992) Polymerase-chain-reaction-based analysis of polymorphism in the HLA-B gene. Hum. Immunol. 34: 257-266.

The invention claimed is:

1. A method for determining the presence of the HLA-B*3913 allele in a sample, wherein exon 2 of said allele is defined by SEQ ID NO: 22, and exon 3 of said allele is defined by SEQ ID NO: 23, wherein said method comprises: a) obtaining nucleic acids from the sample, and b) analyzing the nucleic acids for the presence of the allele HLA-B*3913.

2. The method according to claim 1, further comprising amplifying the nucleic acids before said analyzing step (b) to obtain amplified nucleic acids comprising part or all of exon 2 and/or part or all of exon 3 of said allele using at least one suitable pair of primers, wherein in step (b) the amplified nucleic acids are analyzed for the presence of the allele HLA-B*3913.

3. The method according to claim 2, wherein the analysis of the amplified nucleic acids comprises: a) hybridizing the amplified nucleic acids to a set of probes which specifically hybridize to target regions within the nucleic acids, which regions comprise one or more polymorphic nucleotides in at least one of exon 2 or exon 3 of said allele; and b) determining the presence of the HLA-B*3913 allele.

4. The method according to claim 2, wherein said primers comprise at least one nucleotide sequence chosen from SEQ ID NOs: 26 and 27.

5. The method according to claim 3, wherein said probes comprise at least one nucleotide sequence chosen from: SEQ ID NOs: 28-49.

* * * * *